US008828700B2

(12) United States Patent
Lee et al.

(10) Patent No.: US 8,828,700 B2
(45) Date of Patent: Sep. 9, 2014

(54) SSB-POLYMERASE FUSION PROTEINS

(75) Inventors: Jun Lee, San Diego, CA (US); Robert Potter, San Marcos, CA (US); David Mandelman, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 729 days.

(21) Appl. No.: 12/326,048

(22) Filed: Dec. 1, 2008

(65) Prior Publication Data

US 2010/0075382 A1    Mar. 25, 2010

Related U.S. Application Data

(63) Continuation of application No. 11/222,029, filed on Sep. 9, 2005, now abandoned.

(51) Int. Cl.
*C12N 9/12* (2006.01)
*C12Q 1/68* (2006.01)
*C12N 15/62* (2006.01)

(52) U.S. Cl.
CPC ............. *C12N 15/62* (2013.01); *C12Q 1/6848* (2013.01); *C12N 9/1252* (2013.01)
USPC ........... 435/194; 435/183; 435/69.7; 530/350

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 5,118,801 A | 6/1992 | Lizardi et al. |
| 5,185,444 A | 2/1993 | Summerton et al. |
| 5,188,934 A | 2/1993 | Menchen et al. |
| 5,312,728 A | 5/1994 | Lizardi et al. |
| 5,366,860 A | 11/1994 | Bergot et al. |
| 5,378,841 A | 1/1995 | Summerton |
| 5,436,149 A | 7/1995 | Barnes |
| 5,449,603 A | 9/1995 | Nielson et al. |
| 5,466,591 A | 11/1995 | Abramson et al. |
| 5,470,967 A | 11/1995 | Huie |
| 5,538,848 A | 7/1996 | Livak et al. |
| 5,605,824 A | 2/1997 | Nielson et al. |
| 5,614,365 A | 3/1997 | Tabor et al. |
| 5,646,019 A | 7/1997 | Nielson et al. |
| 5,677,152 A | 10/1997 | Birch et al. |
| 5,693,502 A | 12/1997 | Gold et al. |
| 5,698,685 A | 12/1997 | Summerton et al. |
| 5,719,262 A | 2/1998 | Buchardt et al. |
| 5,763,173 A | 6/1998 | Gold et al. |
| 5,773,257 A | 6/1998 | Nielson et al. |
| 5,773,258 A | 6/1998 | Birch et al. |
| 5,795,762 A | 8/1998 | Abramson et al. |
| 5,800,996 A | 9/1998 | Lee et al. |
| 5,817,781 A | 10/1998 | Swaminathan |
| 5,834,285 A | 11/1998 | Comb et al. |
| 5,847,162 A | 12/1998 | Lee et al. |
| 5,863,727 A | 1/1999 | Lee et al. |
| 5,874,557 A | 2/1999 | Gold et al. |
| 5,925,517 A | 7/1999 | Tyagi et al. |
| 5,936,087 A | 8/1999 | Benson et al. |
| 5,945,526 A | 8/1999 | Lee et al. |
| 5,948,666 A | 9/1999 | Callen et al. |
| 5,972,603 A | 10/1999 | Bedford et al. |
| 5,990,479 A | 11/1999 | Weiss et al. |
| 6,008,379 A | 12/1999 | Benson et al. |
| 6,020,130 A | 2/2000 | Gold et al. |
| 6,020,481 A | 2/2000 | Benson et al. |
| 6,051,719 A | 4/2000 | Benson et al. |
| 6,127,121 A | 10/2000 | Meyer et al. |
| 6,140,500 A | 10/2000 | Yan et al. |
| 6,143,877 A | 11/2000 | Meyer et al. |
| 6,174,670 B1 | 1/2001 | Wittwer et al. |
| 6,180,372 B1 | 1/2001 | Franzen |
| 6,183,967 B1 | 2/2001 | Jayasena et al. |
| 6,183,997 B1 | 2/2001 | Hogrefe |
| 6,183,998 B1 | 2/2001 | Ivanov et al. |
| 6,191,278 B1 | 2/2001 | Lee et al. |
| 6,207,392 B1 | 3/2001 | Weiss et al. |
| 6,214,557 B1 | 4/2001 | Barnes et al. |
| 6,265,193 B1 | 7/2001 | Brandis et al. |
| 6,270,967 B1 | 8/2001 | Whitcombe et al. |
| 6,271,024 B1 | 8/2001 | Sve et al. |
| 6,316,202 B1 | 11/2001 | Barnes et al. |
| 6,333,159 B1 | 12/2001 | Barnes et al. |
| 6,333,183 B1 | 12/2001 | Evans et al. |
| 6,472,186 B1 | 10/2002 | Quintanar et al. |
| 6,482,615 B2 | 11/2002 | Tal et al. |
| 6,489,150 B1 | 12/2002 | Mathur |

(Continued)

FOREIGN PATENT DOCUMENTS

| | | |
|---|---|---|
| EP | 1154017 | 11/2001 |
| EP | 0547359 | 3/2002 |

(Continued)

OTHER PUBLICATIONS

She et al., Gen bank Accession AAK42515, Jun. 2004.*
Hopfner et al., UniProt Accession P56689, Oct. 2004.*
U.S. Appl. No. 11/222,029, Office Action Mailed Feb. 1, 2008.
U.S. Appl. No. 11/222,029, Office Action Mailed Aug. 24, 2007.
U.S. Appl. No. 11/222,029, Response to Office Action Mailed Nov. 26, 2007.
Bochkarev, A. et al., "Structure of single-stranded-DNA-binding domain of replication protein a bound to DNA", *Nature* vol. 385, Nature Publishing Group 1997, 176-181.
Bochkareva, E. et al., ""The RPA32 Subunit of Human Replication Protein A contains a Single-Stranded DNA-binding Domain"", *J. Biol. Chem 273*: American Society for Biochemistry and Molecular Biology 1998, 3932-3947.
Bult, C. J. et al., "Complete Genome Sequence of the Methanogenic Archaeon, *Methanococcus jannaschii*", *Science 273*: American Association for the Advancement of Science 1996, 1058-1073.
Bult, C J., "NCBI Entrez, GenBank Report, accession No. F64444", 1996.
Chedin, Frederic et al., "Novel Homologs of Replication Protein A in Archaea: Implications for the Evolution of ssDNA-Binding Proteins", *Trends in Biochemical Science (TIBS)* vol. 23, No. 8, Elsevier Science, Ltd. Aug. 1998, 273-277.

(Continued)

*Primary Examiner* — Richard Hutson

(57) ABSTRACT

Fusion proteins comprising a single strand DNA binding protein and a nucleic acid polymerase (e.g. DNA polymerase or reverse transcriptase). These high fidelity proteins are suitable for use in nucleic acid amplification methods, including the polymerase chain reaction (PCR).

17 Claims, 1 Drawing Sheet

(56) References Cited

U.S. PATENT DOCUMENTS

| | | | |
|---|---|---|---|
| 6,492,511 B2 | 12/2002 | Callen et al. | |
| 6,503,729 B1 | 1/2003 | Bult et al. | |
| 6,524,830 B2 | 2/2003 | Kopf-Sill | |
| 6,569,627 B2 | 5/2003 | Wittwer | |
| 6,627,424 B1* | 9/2003 | Wang | 435/194 |
| 6,640,891 B1 | 11/2003 | Oldenburg | |
| 6,673,585 B1 | 1/2004 | Querellou et al. | |
| 6,787,338 B2 | 9/2004 | Wittwer et al. | |
| 6,814,934 B1 | 11/2004 | Higuchi | |
| 6,852,832 B1 | 2/2005 | Kowalczykowski et al. | |
| 7,541,170 B2* | 6/2009 | Wang et al. | 435/194 |
| 7,666,591 B2* | 2/2010 | Kowalczykowski et al. | 435/6 |
| 2003/0022162 A1 | 1/2003 | Hatakeyama | |
| 2003/0092018 A1 | 5/2003 | Chatterjee et al. | |
| 2003/0162201 A1 | 8/2003 | Chatterjee et al. | |
| 2003/0207266 A1 | 11/2003 | Chen et al. | |
| 2003/0228616 A1 | 12/2003 | Arezi et al. | |
| 2004/0002076 A1 | 1/2004 | Wang et al. | |
| 2004/0005573 A1 | 1/2004 | Fuller et al. | |
| 2004/0180342 A1 | 9/2004 | Haseltine et al. | |
| 2004/0219558 A1 | 11/2004 | Vander Horn et al. | |
| 2005/0164265 A1 | 7/2005 | Kowalczykowski et al. | |
| 2007/0059713 A1 | 3/2007 | Lee et al. | |
| 2007/0092896 A1 | 4/2007 | Shigemori et al. | |
| 2010/0159527 A1 | 6/2010 | Martin et al. | |

FOREIGN PATENT DOCUMENTS

| | | |
|---|---|---|
| EP | 0745676 | 7/2003 |
| EP | 06795956.9 | 9/2006 |
| EP | 1836319 | 9/2012 |
| EP | 1934372 | 2/2013 |
| JP | 2008-529757 | 9/2006 |
| WO | 92/20702 | 11/1992 |
| WO | 97/45539 | 12/1997 |
| WO | 98/22489 | 5/1998 |
| WO | 99/14226 | 3/1999 |
| WO | 00/39352 | 7/2000 |
| WO | 00/55307 | 9/2000 |
| WO | 01/14568 | 3/2001 |
| WO | 01/38584 | 5/2001 |
| WO | 01/92501 A1 | 12/2001 |
| WO | WO-01/92501 | 12/2001 |
| WO | WO-01/92501 A1 | 12/2001 |
| WO | 03/046149 A2 | 6/2003 |
| WO | 03/046149 A3 | 6/2003 |
| WO | WO-03/046149 A2 | 6/2003 |
| WO | WO-03/046149 A3 | 6/2003 |
| WO | WO-2007029200 A2 | 3/2007 |
| WO | 2007/020125 A2 | 5/2007 |
| WO | WO-2007/050125 A2 | 5/2007 |

OTHER PUBLICATIONS

Cubeddu, L. et al., """Structural and functional characterisatiion of *Sulfolobus solfataricus* SSB and its interaction with DNA"""", *FASEB Summer Research Conference* Federation of American Socities for Experimental Biology 2002 , 14.

Cubeddu, L. et al., "Structural and calorimetric studies of an archael single-stranded DNA binding protein", *European Conference of Current Trends in Microcalorimetry* Applications of Biocalorimetry (ABC III) abstract, 1 pg., Dublin, Ireland Aug. 27-30, 2002 , 14.

Fairman, M. P. et al., """Cellular factors required for multiple stages of SV40 DNA replication in vitro"""", *The EMBO Journal 7*: IRL Press Ltd. 1988 , 1211-1218.

Gomes, X. V. et al., """Functional Domains of the 70-Kilodalton Subunit of Human Replication Protein A"""", *Biochemistry 35*: IRL, American Chemical Society 1996 , 10558-10568.

Haseltine, C. A. et al., "A Distinctive Single-Stranded DNA Binding Protein from the Archaeon *Sulfolobus solfataricus*", *Mol. Microbiol.* 43(6) 2002 , 1505-1515.

Henricksen, C. A. et al., """Phosphorylation of human replication protein A by the DNA-dependent protein kinase is involved in the modulation of DNA replication"""", *Nucleic Acids Res. 24*: Oxford University Press 1996 , 3107-3112.

Inoue, Jin et al., "Improvements of Rolling Circle Amplification (RCA) Efficiency and Accuracy Using *Thermus thermophilus* SSB Mutant Protein", *Nucelic Acids Research* vol. 34, No. 9 e69 Apr. 19, 2006 , 1-9.

Kelly, Thomas J. et al., "Identification and Characterization of a Single-Stranded DNA-Binding Protein From the Archaeon *Methanococcus jannaschii*", *Proceedings of the National Academy of Sciences (PNAS)* vol. 95, National Academy of Sciences of the USA Dec. 1998 , 14634-14639.

Kerr, I. D. et al., """Insights into ssDNA recognitionby OB fold from a structural and thermodynamic study of *Sulfolobus* SSB protein"""", *EMBO J. 22*: Oxford University Press 2003 , 2561-2570.

Kerr, I. D. et al., """Overexpression,purification, crystallization and data collection of a single-stranded DNA-binding protein from *Sulfolobus solfataricus*"""", *Acta Cryst. D Biol. crystallogr. 57*: International Union of Crystallography 2001 , 1290-1292.

Kim, C. et al., "Binding Properties of Replication Protein A from Human and Yeast Cells", *Mol. Cell. Biol.* vol. 12, American Society for Microbiology 1992 , 3050-3059.

Kim, C. et al., "Interactions of Human Replication Protein A with Oligonucleotides", *Biochemistry* vol. 33, American Chemical Society 1994 , 14197-14206.

Klenk, H. P. et al., "The Complete Genome Sequence of the Hyperthermophilic, Sulphate-Reducing Archaeon *Archaeoglobus fulgidus*", *Nature* 390 1997 , 364-370.

Lin, Yi-Ling et al., "The Evolutionarily Conserved Zinc Finger Motif in the Largest Subunit of Human Replication Protein A is Required for DNA Replication and Mismatch Repair but not for Nucleotide Excision Repair", *The Journal of Biological Chemistry* vol. 273, American Society for Biochemistry and Molecular Biology Jan. 15, 1998 , 1453-1461.

Lohman, T. M. et al., """"*Escherichia coli* Single-stranded DNA-Binding protein: Multiple DNA-Binding Modes and Cooperativities"""", *Annu. Rev. Biochem. 63*: Annual Reviews, Inc. 1994 , 527-570.

Ngo, J. T. et al., "Computational Complexity, Protein Structure Prediction, and the Levinthal Paradox", *The Protein Folding Problem and Tertiary Structure Prediction*, Mertz et al. (editors), Birkhauser 1994 , 433, 492-495.

Philipova, D. et al., """A hierarchy of SSB promoters in replication protein A"""", *Genes Dev. 10*: Cold Spring Harbor Laboratory Press 1996 , 2222-2233.

Sancar, A. et al., """Sequences of the ssb gene and protein"""", *Proceedings of the National Academy of Sciences (PNAS)* vol. 78, National Academy of Sciences 1981 , 4274-4278.

Shamoo, Y. et al., "Crystal structure of a replication fork single-stranded DNA binding protein (T4 gp32) complexed to DNA", *Nature* vol. 376, Nature Publishing Group 1995 , 362-366.

She, Q. et al., "The complete genome of the crenarchaeon *Sulfolobus solfataricus* P2", *Proceedings of the National Academy of Sciences (PNAS)* 98(14) Jul. 3, 2001 , 7835-7840.

Smith, D. R. et al., """Complete Genome Sequence of *Methanobacterium thermoautotrophicum* Δh: Functional Analysis and Comparative Genomics"""", *J. Bacteriol. 179*: American Society for Microbiology 1996 , 7135-7155.

Sreenivas, K. et al., """An Archaeal DNA Binding Protein from Thermophilic *Sulfolobus acidocaldarius* Forms Different Types of Complexes with DNA"""", *Biochem.Mol. Biol. Int. 44*: Academic Press Australia 1998 , 269-282.

Wadsworth, R. I. et al., "Identification and Properties of teh Crenarchaeal Single Stranded DNA Binding Protein from *Sulfolobus solfataricus*", *Nucl. Acids Res.* 29 2001 , 914-920.

Wold, M. S. et al., """Replication Protein A: A Heterotrimeric, Single-Stranded DNA-Binding Protein Required for Eukaryotic DNA Metabolism"""", *Annu. Rev. Biochem. 66*: Annual Reviews, Inc. 1997 , 61-92.

Antony, T "Selectivity of Polyamines on the Stability of RNA-DNA Hybrids Containing Phosphodiester and Phosphorothioate Oligodeoxyribonucleotides", *Biochemistry* vol. 38, No. 33, American Chemical Society Aug. 17, 1999 , 10775-10784.

Balandina, A "The Bacterial Histone-like Protein HU specifically recognizes similar structures in all nucleic acids DNA, RNA, and their hybrids", *The Journal of Biological Chemistry* vol. 277, No. 31,

(56) References Cited

OTHER PUBLICATIONS

The American Society for Biochemistry and Molecular Biology, Inc., USA, Aug. 2, 2002, 27622-27628.

Conrad, C "Both N-terminal catalytic and C-terminal RNA binding domain contribute to substrate specificity and cleavage site selection of RNase III", *FEBS Letters* vol. 509, No. 1, Elsevier Science B.V., Nov. 30, 2001, 53-58.

Daimon, K "Three Proliferating Cell Nuclear Antigen-Like Proteins Found in the Hyperthermophilic Archaeon *Aeropyrum pernix*: Interactions with the Two DNA Polymerases", *Journal of Bacteriology* vol. 184, No. 3, American Society for Microbiology, Feb. 2002, 687-694.

Dostal, L "Partial B-to-A DNA Transition upon Minor Groove Binding of Protein Sac7d Monitored by Raman Spectroscopy", *Biochemistry* vol. 43, No. 30, American Chemical Society, Aug. 3, 2004, 9600-9609.

EP06717401.1, "Office Action", mailed Nov. 9, 2009, 7 pages.
EP06717401.1, "Office Action", mailed Sep. 30, 2010, 8 pages.
EP06717401.1, "Response to Nov. 9, 2009 Office Action", filed Aug. 23, 2010, 3 pages.
EP06717401.1, "Response to Sep. 30, 2010 Office Action", filed Mar. 30, 2011, 7 pages.
EP06795956.9, "Extended European Search Report", mailed Sep. 16, 2009, 8 pages.
EP06795956.9, "Office Action", mailed Jan. 15, 2010, 1 page.
EP06795956.9, "Response to Jan. 15, 2010 Office Action", filed Jul. 22, 2010, 2 pages.
EP09016058.1, "Extended European Search Report", mailed Oct. 4, 2010, 18 pages.
EP09016058.1, "Response to Nov. 8, 2010 Communication Pursuant to Rule 69 EPC", filed May 2, 2011, 3 pages.
EP090160581, "Partial European Search Report", mailed Jun. 11, 2010, 6 pages.

Fitz-Gibbon, S "Genome Sequence of the Hypertherophilic Crenarchaeon *Pyrobaculum aerophilum*", *PNAS* vol. 99, No. 2, Jan. 22, 2002, 984-989.

Guagliardi, A "Annealing of Complementary DNA Strands Above the Melting Point of the Duplex Promoted by an Archael Protein", *Journal of Molecular Biology* vol. 267, No. 4, London, Great Britain, Apr. 11, 1997, 841-848.

Hardy, C "Biochemical characterization of DNA-binding proteins from *Pyrobaculum aerophilum* and *Aeropyrum pernix*", *Extremophiles: Life Under Extreme Conditions* vol. 12, No. 2, Mar. 2008, 235-246.

Kawarabayasi, Y "Complete Genome Sequence of an Aerobic Hyper-thermophilic Crenarchaeon, *Aeropyrum pernix* K1", *DNA Research* vol. 6, No. 2, Universal Academy Press, Japan, Apr. 30, 1999, 83-101.

Kawasaki, A. M. "Uniformly Modified 2'-Deoxy-2'-fluroro Phosphorothioate Oligonucleotides as Nuclease-Resistant Antisense Compounds with High Affinity and Specificity for RNA Targets", *Journal of Medicinal Chemistry* vol. 36, No. 7, American Chemical Society, Washington, US, Apr. 2, 1993, 831-841.

Oshima, R. G. "Single-Stranded DNA Binding Protein Facilitates Amplification of Genomic Sequences by PCR", *BioFeedback* vol. 13, No. 128, Circle Reader Service, Jan. 1, 1992, 188.

She, Q. "The complete genome of the crenarchaeon *Sulfolobus solfataricus* P2", *PNAS* vol. 98, No. 14, Jul. 3, 2001, 7835-7840.

Singleton, M R. "Conformational Changes Induced by Nucleotide Binding in Cdc6/ORC From *Aeropyrum pernix*", *Journal of Molecular Biology* vol. 343, No. 3, Elsevier Ltd., London, GB, Oct. 22, 2004, 547-557.

Sun, S. "Biochemical and Structural Characterization of Interactions between DNA Polymerase and Single-Stranded DNA Binding Protein in Bacteriophage RB69", at URL=http://aca.hwi.buffalo.edu/ACA05/abstracts/text/W0359.pdf downloaded Sep. 2, 2009 May 29, 2009, 1 page.

Sun, S. "Biochemical Characterization of Interactions between DNA Polymerase and Single-stranded DNA-binding Protein in Bacteriophage RB69", *The Journal of Biological Chemistry* vol. 278, No. 6, The American Society for Biochemistry and Molecular Biology, Inc., USA, Feb. 7, 2003, 3876-3881.

Sun, S. "Structure and Enzymatic Properties of a Chimeric Bacteriophage RB69 DNA Polymerase and Single-Stranded DNA Binding Protein With Increased Processivity", *PROTEINS: Structure, Function and Bioinformatics* vol. 65, No. 1, Wiley InterSciene, Oct. 1, 2006, 231-238.

U.S. Appl. No. 11/222,029, "Response to Aug. 24, 2007 Non-Final Office Action", filed Nov. 26, 2007, 16 pages.
U.S. Appl. No. 12/545,782, "Final Office Action", mailed Apr. 21, 2011, 12 pages.
U.S. Appl. No. 12/545,782, "Non-Final Office Action", mailed Oct. 13, 2010, 12 pages.

Wang, Y. "A novel strategy to engineer DNA polymerases for enhanced processivity in vitro", *Nucleic Acids Research* vol. 32, No. 3, Oxford University Press, Jan. 1, 2004, 1197-1207.

White, M F. "Holding it together: chromatin in the Archaea", *TRENDS in Genetics* vol. 18, No. 12, Elsevier Science, B. V. Amsterdam, NL, Dec. 2002, 621-626.

Afonina, I. A. et al., "Minor Groove Binder-Conjugated DNA Probes for Quantitative DNA Detection by Hybridization-Triggered Fluorescence", *BioTechniques*, vol. 32, 2002; pp. 940-949.

Alba, et al., "Protein family review: Replicative DNA polymerases", *Genome Biology*, vol. 2, No. 1, Jan. 12, 2001; pp. 3002.1-3002.4.

Arezi, Bahram et al., "Amplification efficiency of thermostable DNA polymerases", *Analytical Biochemistry*, vol. 321, Issue 2, Oct. 15, 2003; pp. 226-235.

Barnes "The Fidelity of Taq Polymerase Catalyzing PCR is Improved by an N-Terminal Deletion", *Gene*, vol. 112, No. 1, Mar. 1, 1992; pp. 29-35.

Baumann, Herbert et al., "Solution structure and DNA-binding properties of a thermostable protein from the archaeon *Sulfolobus solfataricus*", *Nature Structural & Molecular Biology*, vol. 1, 1994; pp. 808-819.

Blain, et al., "Nuclease Activities of Moloney Murine Leukemia Virus Reverse Transcriptase", *The Journal of Biological Chemistry*, vol. 268, No. 31, Nov. 5, 1993; pp. 23585-23592.

Böhlke, K et al., "PCR performance of the B-type DNA polymerase from the thermophilic euryarchaeon *Thermococcus aggregans* improved by mutations in the Y-GG/A motif", *Nucleic Acids Research*, vol. 28, No. 20, Oxford University Press, Oct. 15, 2000; pp. 3910-3917.

Braithwaite, D K. et al., "Compilation, alignment, and phylogenetic relationships of DNA polymerases", *Nucleic Acids Research*, vol. 21, No. 4, Feb. 25, 1993; pp. 787-802.

Briselden, Ann Marie et al., "Evaluation of Affirm VP Microbial Identification Test for *Gardnerella vaginalis* and *Trichomonas vaginalis*", *Journal of Clinical Microbiology*, vol. 32, No. 1, Jan. 1994; pp. 148-152.

Büning, H et al., "The histidine tail of recombinant DNA binding proteins may influence the quality of interaction with DNA", *Analytical Biochemistry*, vol. 234, Issue 2, Feb. 15, 1996; pp. 227-230.

Constans, A , "Some Like It Hot: A Thermal Cycler Roundup", *The Scientist*, vol. 15, Issue 24, Dec. 10, 2001; 4 pages.

Crasto, Chiquito J. et al., "LINKER: a program to generate linker sequences for fusion proteins", *Protein Engineering Design & Selection*, vol. 13, Issue 5, Oxford University Press, May 2000; pp. 309-312.

Derbyshire, Victoria et al., "[28] Structure-function analysis of 3'→5'-exonuclease of DNA polymerases", *Methods in Enzymology*, vol. 262, Academic Press, Inc., 1995; pp. 363-385.

Filee, et al., "Evolution of DNA Polymerase Families: Evidences for Multiple Gene Exchange Between Cellular and Viral Proteins", *Journal of Molecular Evolution*, vol. 54, No. 6, 2002; pp. 763-773.

Fogg, Mark J. et al., "Structural basis for uracil recognition by archaeal family B DNA polymerases", *Nature Structural Biology*, vol. 9, No. 12, Dec. 2002; pp. 922-927.

Freier, S et al., "The ups and downs of nucleic acid duplex stability: structure-stability studies on chemically-modified DNA:RNA duplexes", *Nucleic Acids Research*, vol. 25, No. 22, 1997; pp. 4429-4443.

(56) References Cited

OTHER PUBLICATIONS

Fujimori, Shizuyoshi et al., "Enantio-DNA Recognizes Complimentary RNA but Not Complementary DNA", *J. Am. Chem. Soc.*, vol. 112, 1990; pp. 7436-7438.

Gao, Yi-Gui et al., "The crystal structure of the hyperthermophile chromosomal protein Sso7d bound to DNA", *Nature Structural Biology*, vol. 5, No. 9, Nature America Inc., Sep. 1998; pp. 782-786.

Garbesi, Anna et al., "L-DNAs as potential antimessenger oligonucleotides: a reassessment", *Nucleic Acids Research*, vol. 21, No. 18, 1993; pp. 4159-4165.

Genbank, , "paREP4 [*Pyrobaculum aerophilum* str. IM2].", Accession No. AAL64814, Downloaded at URL: http://www.ncbi.nlm.nih.gov/protein/AAL64814 on Feb. 21, 2013, Feb. 25, 2009; 1 page.

Grönlund, Hans , "Formation of disulfide bonds and homodimers of the major cat allergen Fel d 1 equivalent to the natural allergen by expression in *Escherichia coli*", *The Journal of Biological Chemistry*, vol. 278, No. 41, The American Society for Biochemistry and Molecular Biology, Inc., Oct. 10, 2003; pp. 40144-40151.

Han, M. et al., "Quantum-dot-tagged microbeads for multiplexed optical coding of biomolecules", *Nature Biotechnology*, vol. 19, Jul. 2001; pp. 631-635.

Heid, et al., "Real Time Quantitive PCR", *Genome Research*, vol. 6, No. 10, Cold Spring Harbor Laboratory Press, Woodbury, NY, Oct. 1996, 986-994.

Ignatov, K. B. et al., "Substitution of Asn for Ser543 in the large fragment of Taq DNA polymerase increases for efficiency of synthesis of long DNA molecules", *FEBS Letters*, vol. 425, Federation of European Biochemical Societies, 1998; pp. 249-250.

Ito, et al., "Compilation and alignment of DNA polymerase sequences", *Nucleic Acids Research*, vol. 19, No. 15, 1991; pp. 4045-4057.

Jones, et al., "Synthesis and Binding Properties of Pyrimidine Oligodeoxynucleoside Analogs Containing Neutral Phosphodiester Replacements.", *J. Org. Chem.*, vol. 58, 1993, pp. 2983-2991.

Kaiser, M. W. et al., "A Comparison of Eubacterial and Archaeal Structure-specific 5'-Exonucleases", *The Journal of Biological Chemistry*, vol. 274, No. 30, The American Society for Biochemistry and Molecular Biology, Inc., USA, 1999; pp. 21387-21394.

Kamashev, D et al., "The histone-like protein HU binds specifically to DNA recombination and repair intermediates", *The EMBO Journal*, vol. 19, No. 23, European Molecular Biology Organization, Dec. 1, 2000; pp. 6527-6535.

Kellogg, D. E. et al., "TaqStart Antibody: "Hot Start" PCR Facilitated by a Neutralizing Monoclonal Antibody Directed Against Taq DNA Polymerase", *Bio techniques*, vol. 16, No. 6, BPA international, 1994; pp. 1134-1137.

Kermekchiev, Milko B. et al., "Cold-sensitive mutants of Taq DNA polymerase provide a hot start for PCR", *Nucleic Acids Research*, vol. 31, No. 21, Oxford University Press, Nov. 1, 2003; pp. 6139-6147.

Kong, Huimin et al., "Characterization of a DNA polymerase from the hyperthermophile archaea *Thermococcus litoralis* Vent DNA polymerase, steady state kinetics, thermal stability, processivity, strand displacement, and exonuclease activities", *The Journal of Biological Chemistry*, vol. 268, No. 3, The American Society for Biochemistry and Molecular Biology, Inc, Jan. 25, 1993; pp. 1965-1975.

Kricka, Larry , "Nucleic Acid Hybridization Test Formats: Strategies and Applications", *Nonisotopic DNA Probe Techniques*, Academic Press, Inc., 1992; pp. 3-28.

Kuroita, et al., "Structural mechanism for coordination of proofreading and polymerase activies in archael DNA polymerases", *Journal of Molecular Biology*, vol. 351, Issue 2, Aug. 12, 2005; pp. 291-298.

Lawyer, et al., "Isolation, Characterization, and Expression in *Escherichia coli* of the DNA Polymerase Gene from *Thermus aquaticus*", *The Journal of Biological Chemistry*, vol. 264, No. 11, Apr. 15, 1989; pp. 6427-6437.

Lin, Z et al., "Multiplex of Genotype Determination at a Large Number of Gene Loci", *Proceedings of the National Academy of Sciences of the United States*, vol. 93, No. 6, Genetics, USA,, Mar. 1996; pp. 2582-2587.

Livak, Kenneth J. et al., "Oligonucleotides with Fluorescent Dyes at Opposite Ends Provide a Quenched Probe System Useful for Detecting PCR Product and Nucleic Acid Hybridization", *PCR Methods and Applications*, vol. 4, 1995; pp. 357-362.

Mai, Viet Q. et al., "Small Abundant DNA Binding Proteins from the Thermoacidophillic Archaeon *Sulfolobus shibatae* Constrain Negative DNA Supercoils", *Journal of Bacteriology*, vol. 180, No. 9, American Society for Microbiology, May 1998; pp. 2560-2563.

McAfee, James G. et al., "Gene Cloning, Expression and Characterization of the Sac7 Proteins from the Hyperthermophile *Sulfolobus acidocaldarius*", *Biochemistry*, vol. 34, No. 31, American Chemical Society, 1995; pp. 10063-10077.

Medintz, Igor L. et al., "Quantum dot bioconjugates for imaging, labelling and sensing", *Nature Materials*, vol. 4, Jun. 2005; pp. 435-446.

Mittal, Vivek , "Appendix 10: DNA Array Technology", *Molecular Cloning: A Laboratory Manual*, Third Edition, vol. 3, Cold Spring Harbor Laboratory Press, New York, 2001; pp. A10.1-A10.19.

Moore, Pete , "PCR: Replicating success", *Nature*, vol. 435, May 12, 2005; pp. 235-238.

Motz, M et al., "Elucidation of an Archaeal Replication Protein Network to Generate Enhanced PCR Enzymes", *The Journal of Biological Chemistry*, vol. 277, No. 18, The American Society for Biochemistry and Molecular Biology, Inc., May 3, 2002; pp. 16179-16188.

Nielsen, P. et al., "Sequence-Selective Recognition of DNA by Strand Displacement with a Thymine-Substituted Polyamide", *Science*, vol. 254, Dec. 6, 1991; pp. 1497-1500.

Pavlov, et al., "Recent developments in the optimization of thermostable DNA polymerases for efficient applications", *Trends in Biotechnology*, vol. 22, Issue 5, May 2004; pp. 253-260.

PCT/US2006/000191; International Preliminary Report on Patentability mailed Jul. 19, 2007; 16 pages.

PCT/US2006/000292; International Preliminary Report on Patentability mailed Jul. 19, 2007; 11 pages.

Pereira, Suzette et al., "Archaeal nucleosomes", *Proceedings of the National Academy of Sciences of the United States of America*, Microbiology, vol. 94, No. 23, Nov. 11, 1997; pp. 12633-12637.

Pritham, et al., "Continuous Flouresecent Monitoring of Rapid Cycle Polymerase Chain Reaction", *Clinical Ligand Assay.*, vol. 21, No. 4, 1998; pp. 404-412.

Robinson, Howard et al., "The hyperthermophile chromosomal protein Sac7d sharply kinks DNA", *Nature*, vol. 392, Macmillan Publishers Ltd, Mar. 12, 1998; pp. 202-205.

Rychlik, W et al., "Optimization of the annealing temperature for DNA amplification in vitro", *Nucleic Acids Research*, vol. 18, No. 21, Oxford University Press, Nov. 11, 1990; pp. 6409-6412.

Sambrook, Joseph et al., *Molecular Cloning: A Laboratory Manual*, Third Edition, vol. 1, Cold Spring Harbor Laboratory Press, New York, 2001; pp. 6.33-6.58.

Sambrook, Joseph et al., *Molecular Cloning: A Laboratory Manual*, Third Edition, vol. 2, Chapter 9, Protocols 13-16, Cold Spring Harbor Laboratory Press, New York, 2001; pp. 9.62-9.75.

Sambrook, Joseph et al., "Cycle Sequencing: Dideoxy-mediated Sequencing Reactions Using PCR and End-Labeled Primers", *Molecular Cloning: A Laboratory Manual*, Third Edition, vol. 2, Chapter 12, Protocol 6, Cold Spring Harbor Laboratory Press, New York, 2001; pp. 12.51-12.60 and 12.94-12.114.

Sambrook, Joseph et al., "In Vitro Amplification of DNA by the Polymerase Chain Reaction", *Molecular Cloning: A Laboratory Manual*, Third Edition, vol. 2, Chapter 8, Cold Spring Harbor Laboratory Press, New York, 2001 ; pp. 8.1-8.126.

Santalucia, John , "A unified view of polymer, dumbbell and oligonucleotide DNA nearest-neighbor thermodynamics", *Biochemistry*, vol. 95, Proceedings of the National Academy of Sciences, USA, Feb. 1998; pp. 1460-1465.

Shandilya, H et al., "Thermophilic bacterial DNA polymerases with reverse-transcriptase activity", *Extremophiles*, vol. 8, No. 3, Springer-Verlag, Apr. 9, 2004; pp. 243-251.

(56) References Cited

OTHER PUBLICATIONS

Shehi, Erlet et al., "Thermal Stability and DNA Binding Activity of a Variant Form of the Sso7d Protein from the Archeon *Sulfolobus solfataricus* Truncated at Leucine 54", *Biochemistry*, vol. 42, No. 27, American Chemical Society, Jul. 15, 2003; pp. 8362-8368.

Shi, M. et al., "Enabling Large-Scale Pharmacogenetic Studies by High-Throughput Mutation Detection and Genotyping Tehnologies", *Clinical Chemistry*, vol. 47, No. 2, 2001; pp. 164-172.

Shuttleworth, G et al., "Recognition of the pro-mutagenic base uracil by family B DNA polymerases from archaea", *Journal of Molecular Biology*, vol. 337, Issue 3, Mar. 26, 2004; pp. 621-634.

Singer, , "UV spectral characteristics and acidic dissociation constants of 280 alkyl bases, nucleosides, and nucleotides", *Practical Handbook of Biochemistry and Molecular Biology*, 1989; pp. 385-394.

Southworth, M et al., "Cloning of thernostable DNA polymerases from hyperthermophilic marine Archaea with emphasis on *Thermococcus* sp. 9°N-7 and mutations affecting 3'-5'exonuclease activity", *Proceedings of the National Academy of Sciences of the United States of America*, Biochemistry, vol. 93, No. 11, May 28, 1996; pp. 5281-5285.

Steitz, Thomas , "DNA Polymerases: Structural Diversity and Common Mechanisms", *The Journal of Biological Chemistry*, vol. 274, No. 25, 1999; pp. 17395-17398.

Stemmer, W. P. et al., "Single-Step Assembly of a Gene and Entire Plasmid from Large Numbers of Oligodeoxyribonucleotides", *Gene*, vol. 164, 1995; pp. 49-53.

Stirchak, Eugene et al., "Uncharged stereoregular nucleicacid analogues. 1. Synthesis of a Cytosine containino oliaomerwith carbamate intemucleoside linkages", *The Journal of Organic Chemistry*, vol. 52, No. 19, American Chemical Society, 1987; pp. 4202-4206.

Takagi Masahiro et al., "Characterization of DNA polymerase from *Pyrococcus* sp. strain KOD1 and its application to PCR", *Applied and Environmental Microbiology*, vol. 63, No. 11, American Society for Microbiology, Nov. 1997; pp. 4504-4510.

Tatusova, Tatiana et al., "Erratum to "BLAST 2 Sequences, a new tool for comparing protein and nucleotide sequences"", *FEMS Microbiology Letters*, vol. 177, Issue 1, Blackwell Publishing Ltd., Aug. 1, 1999; pp. 187-188.

Telesnitsky, et al., "RNase H Domain Mutations Affect the Interaction Between Moloney Murine Leukemia Virus Reverse Transcriptase and Its Primer-Template", *Proceedings of the National Academy of Sciences*, vol. 90, No. 4, Feb. 15, 1993; pp. 1276-1280.

Urata, Hidehito et al., "Spectroscopic Characterization of Heterochiral DNAs" *Nucleic Acids Symposium Series*, No. 29, 1993; pp. 69-70.

Vainshtein, et al., "Peptide rescue of an N-terminal truncation of the Stoffel fragment of Taq DNA polymerase", *Protein Science*, vol. 5, Issue 9, The Protein Society, Sep. 1996; pp. 1785-1792.

Vasseur, Jean et al., "Oligonucleosides: Synthesis of a Novel Methylhydroxylamine-Linked Nucleoside Dimer and Its Incorporation into Antisense Sequences", *Journal of the American Chemical Society*, vol. 114, American Chemical Society, May 1992; pp. 4006-4007.

Walsh, P. et al., "Sequence analysis and characterization of stutter products at the tetranucleotide repeat locus vWA", *Nucleic Acids Research*, vol. 24, No. 14, 1996; pp. 2807-2812.

Whitcombe, D et al., "Detection of PCR products using self probing amplicons and fluorescence", *Nature Biotechnology*, vol. 17, No. 8, Nature Publishing Group, Aug. 1999; pp. 804-807.

Witt, Armin et al., "DNA Hybridization Test: Rapid Diagnostic Tool for Excluding Bacterial Vaginosis in Pregnant Women with Symptoms Suggestive of Infection", *Journal of Clinical Microbiology*, vol. 40, No. 8, American Society for Microbiology, Aug. 2002; pp. 3057-3059.

Antony, T et al., "Selectivity of Polyamines on the Stability of RNA-DNA Hybrids Containing Phosphodiester and Phosphorothioate Oligodeoxyribonucleotides", *Biochemistry*, vol. 38, No. 33, American Chemical Society, Aug. 17, 1999, 10775-10784.

Balandina, A et al., "The Bacterial Histone-like Protein HU specifically recognizes similar structures in all nucleic acids DNA, RNA, and their hybrids", The Journal of Biological Chemistry, vol. 277, No. 31, The American Society for Biochemistry and Molecular Biology, Inc., USA, Aug. 2, 2002, 27622-27628.

Conrad, C et al., "Both N-terminal catalytic and C-terminal RNA binding domain contribute to substrate specificity and cleavage site selection of RNase III", FEBS Letters, vol. 509, No. 1, Elsevier Science B.V., Nov. 30, 2001, 53-58.

Daimon, K et al., "Three Proliferating Cell Nuclear Antigen-Like Proteins Found in the Hyperthermophilic Archaeon *Aeropyrum pernix*: Interactions with the Two DNA Polymerases", Journal of Bacteriology, vol. 184, No. 3, American Society for Microbiology, Feb. 2002, 687-694.

Dostal, L et al., "Partial B-to-A DNA Transition upon Minor Groove Binding of Protein Sac7d Monitored by Raman Spectroscopy", Biochemistry, vol. 43, No. 30, American Chemical Society, Aug. 3, 2004, 9600-9609.

Fitz-Gibbon, S et al., "Genome Sequence of the Hyptherophilic Crenarchaeon *Pyrobaculum aerophilum*", PNAS, vol. 99, No. 2, Jan. 22, 2002, 984-989.

Guagliardi, A et al., "Annealing of Complementary DNA Strands Above the Melting Point of the Duplex Promoted by an Archael Protein", Journal of Molecular Biology, vol. 267, No. 4, London, Great Britain, Apr. 11, 1997, 841-848.

Hardy, C et al., "Biochemical characterization of DNA-binding proteins from *Pyrobaculum aerophilum* and *Aeropyrum pernix*", Extremophiles: Life Under Extreme Conditions, vol. 12, No. 2,, Mar. 2008, 235-246.

Kawarabayasi, Y et al., "Complete Genome Sequence of an Aerobic Hyper-thermophilic Crenarchaeon, *Aeropyrum pernix* K1", DNA Research, vol. 6, No. 2, Universal Academy Press, Japan, Apr. 30, 1999, 83-101.

Kawasaki, A. M. et al., "Uniformly Modified 2'-Deoxy-2'-fluroro Phosphorothioate Oligonucleotides as Nuclease-Resistant Antisense Compounds with High Affinity and Specificity for RNA Targets", Journal of Medicinal Chemistry, vol. 36, No. 7, American Chemical Society, Washington, US, Apr. 2, 1993, 831-841.

Oshima, R. G. , "Single-Stranded DNA Binding Protein Facilitates Amplification of Genomic Sequences by PCR", BioFeedback, vol. 13, No. 128, Circle Reader Service, Jan. 1, 1992, 188.

She, Q. et al., "The complete genome of the crenarchaeon *Sulfolobus solfataricus* P2", PNAS, vol. 98, No. 14, Jul. 3, 2001, 7835-7840.

Singleton, M R. et al., "Conformational Changes Induced by Nucleotide Binding in Cdc6/ORC From *Aeropyrum pernix*", Journal of Molecular Biology, vol. 343, No. 3, Elsevier Ltd., London, GB, Oct. 22, 2004, 547-557.

Sun, S. et al., "Biochemical and Structural Characterization of Interactions between DNA Polymerase and Single-Stranded DNA Binding Protein in Bacteriophage RB69", at URL=http://aca.hwi.buffalo.edu/ACA05/abstracts/text/W0359.pdf, downloaded Sep. 2, 2009, May 29, 2009, 1 page.

Sun, S. et al., "Biochemical Characterization of Interactions between DNA Polymerase and Single-stranded DNA-binding Protein in Bacteriophage RB69", The Journal of Biological Chemistry, vol. 278, No. 6, The American Society for Biochemistry and Molecular Biology, Inc., USA, Feb. 7, 2003, 3876-3881.

Sun, S. et al., "Structure and Enzymatic Properties of a Chimeric Bacteriophage RB69 DNA Polymerase and Single-Stranded DNA Binding Protein With Increased Processivity", PROTEINS: Structure, Function and Bioinformatics, vol. 65, No. 1, Wiley InterSciene, Oct. 1, 2006, 231-238.

Wang, Y. et al., "A novel strategy to engineer DNA polymerases for enhanced processivity and improved performance in vitro", Nucleic Acids Research, vol. 32, No. 3, Oxford University Press, Jan. 1, 2004, 1197-1207.

White, M F. et al., "Holding it together: chromatin in the Archaea", Trends in Genetics, vol. 18, No. 12, Elsevier Science, B.V. Amsterdam, NL, Dec. 2002, 621-626.

\* cited by examiner

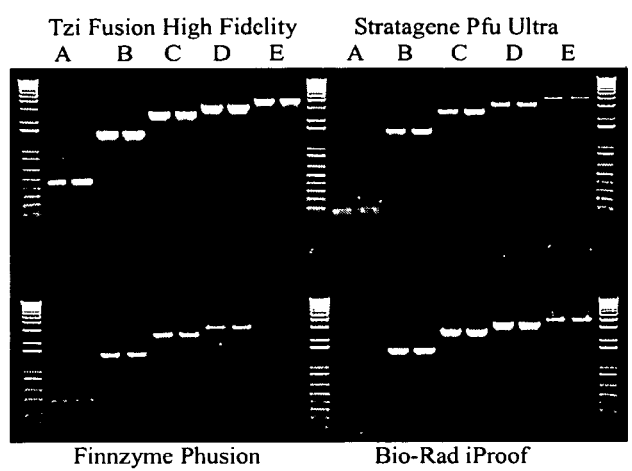

SSB-POLYMERASE FUSION PROTEINS

CROSS REFERENCE TO RELATED APPLICATIONS

The present application is a continuation of U.S. patent application Ser. No. 11/222,029 filed Sep. 9, 2005 now abandoned, the contents of which are entirely incorporated herein by reference.

BACKGROUND OF THE INVENTION

1. Field of the Invention

The present invention provides fusion proteins comprising a single strand DNA binding protein (SSB) and a nucleic acid polymerase, and methods for using such fusion proteins in nucleic acid synthesis reactions.

2. Background of the Invention

DNA polymerases synthesize DNA molecules that are complementary to all or a portion of a nucleic acid template, typically a DNA template. Upon hybridization of a primer to a DNA template to form a primed template, DNA polymerases can add nucleotides to the 3' hydroxyl end sequence of nucleotides of the primer in a template-directed (i.e. depending upon the sequence of nucleotides in the template). Thus, in the presence of deoxyribonucleoside triphosphates (dNTPs) and a primer, a new DNA molecule, complementary to all or a portion of one or more nucleic acid templates, can be synthesized.

DNA polymerases that exhibit increased yield and/or enhanced fidelity (i.e., more accurate template-directed polymerization) are useful in nucleic acid synthesis, amplification and sequencing reaction. The compositions and methods described herein provide such DNA polymerases.

SUMMARY OF THE INVENTION

The present invention provides an isolated or purified single stranded binding protein (SSB)-nucleic acid polymerase fusion protein. In one embodiment, the nucleic acid polymerase is a DNA polymerase. In another embodiment, the nucleic acid polymerse is a reverse transcriptase. The nucleic acid polymerase may be thermostable. In one embodiment, the thermostable DNA polymerase is *Thermococcus zilligi* (Tzi) DNA polymerase. In another embodiment, the SSB is thermostable. In one aspect of this embodiment, the SSB is *Sulfolobus solfataricus* (Sso) SSB.

The present invention also provides a nucleic acid molecule encoding a SSB-nucleic acid polymerase fusion protein. In one embodiment, the nucleic acid polymerase is a DNA polymerase. In another embodiment, the nucleic acid polymerse is a reverse transcriptase. The nucleic acid polymerase may be thermostable. In one embodiment, the thermostable DNA polymerase is *Thermococcus zilligi* (Tzi) DNA polymerase. In another embodiment, the SSB is thermostable. In one aspect of this embodiment, the SSB is *Sulfolobus solfataricus* (Sso) SSB.

An expression vector is also provided which comprises the nucleic acid molecule described above operably linked to a heterologous promoter. The present invention also provides a host cell comprising this expression vector.

The present invention also provides a nucleic acid molecule encoding a *Sulfolobus solfataricus* (Sso) SSB-*Thermococcus zilligi* (Tzi) DNA polymerase fusion protein.

Another embodiment of the invention is a method of increasing the yield of a polymerase reaction on a target nucleic acid comprising contacting the target nucleic acid with a primer which specifically hybridizes thereto, and an isolated or purified SSB-nucleic acid polymerase fusion protein; and incubating the resulting mixture under conditions whereby said primer is extended by said polymerase. In one embodiment, the nucleic acid polymerase is a DNA polymerase. In another embodiment, the nucleic acid polymerse is a reverse transcriptase. The nucleic acid polymerase may be thermostable. In one embodiment, the thermostable DNA polymerase is *Thermococcus zilligi* (Tzi) DNA polymerase. In another embodiment, the SSB is thermostable. In one aspect of this embodiment, the SSB is *Sulfolobus solfataricus* (Sso) SSB.

The present invention also provides an isolated or purified *Sulfolobus solfataricus* (Sso) SSB-*Thermococcus zilligi* (Tzi) polymerase fusion protein.

BRIEF DESCRIPTION OF THE DRAWING

FIG. 1 is a photograph of an agarose gel showing a comparison of Sso SSB-Tzi polymerase fusion protein to PfuUltra (Stratagene), Phusion (Finnzyme) and iProof (Bio-Rad) in PCR target amplification. PCR was performed with 100 ng K562 cell DNA template. Targets tested were A) Rhod 462 bp, B) p53 1494 bp, C) Rhod 2497 bp, D) Rhod 3123 bp, and E) Rhod 3871 bp. Sso SSB Tzi polymerase fusion protein amplified all targets with the greatest yields.

DETAILED DESCRIPTION OF THE INVENTION

The invention is based, in part, on the surprising discovery that yield and/or fidelity of a DNAP can be improved via fusion of a single strand DNA binding protein (SSB) with a DNA polymerase. Described herein are such SSB-DNA polymerase fusion proteins, as well as methods for nucleic acid sequencing, amplification (e.g., PCR) and synthesis using such SSB-DNA polymerase fusion proteins.

DEFINITIONS

The following terms are commonly used by those skilled in the art of molecular biology.

Nucleic acid. In general, a nucleic acid comprises a contiguous series (a.k.a., "strand" and "sequence") of nucleotides joined by phosphodiester bonds. A nucleic acid can be single stranded or double stranded, where two strands are linked via noncovalent interactions between complementary nucleotide bases. A nucleic acid can include naturally occurring nucleotides and/or non-naturally occurring base moieties). A nucleic acid can be ribonucleic acid (RNA, including mRNA) or deoxyribonucleic acid (DNA, including genomic DNA, recombinant DNA, cDNA and synthetic DNA). A nucleic acid can be a discrete molecule such as a chromosome or cDNA molecule. A nucleic acid can also be a segment (i.e. a series of nucleotides connected by phosphodiester bonds) of a discrete molecule.

Template. A template is a single stranded nucleic acid that, when part of a primer-template complex, can serve as a substrate for a DNA polymerase. The template can be DNA (for DNA-directed DNA polymerase) or RNA (for RNA-directed DNA polymerase). A nucleic acid synthesis mixture can include a single type of template, or can include templates having different nucleotide sequences. By using primers specific for particular templates, primer extension products can be made for a plurality of templates in a nucleic acid synthesis mixture. The plurality of templates can be present within different discrete nucleic acids, or can be present within a discrete nucleic acid.

Templates can be obtained, or can be prepared from nucleic acids present in biological sources. (e.g. cells, tissues, body fluids, organs and organisms). Thus, templates can be obtained, or can be prepared from nucleic acids present in bacteria (e.g. species of *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, erwinia, Agrobacterium, Rhizobium* and *Streptomyces*), fungi such as yeasts, viruses (e.g., Orthomyxoviridae, Paramyxoviridae, Herpesviridae, Picornaviridae, Hepadnaviridae, Retroviridae), protozoa, plants and animals (e.g., insects such as *Drosophila* app., nematodes such as *C. elegans*, fish, birds, rodents, porcines, equines, felines, canines and primates, including humans. Templates can also be obtained, or can be prepared from, nucleic acids present in environmental samples such as soil, water and air samples. Nucleic acids can be prepared from such biological and environmental sources using routine methods known by those of skill in the art.

In some embodiments, a template is obtained directly from a biological or environmental source. In other embodiments, a template is provided by wholly or partially denaturing a double-stranded nucleic acid obtained from a biological or environmental source. In some embodiments, a template is a recombinant or synthetic DNA molecule. Recombinant or synthetic DNA can be single stranded or double stranded. If double stranded, the template may be wholly or partially denatured to provide a template. In some embodiments, the template is an mRNA molecule or population of mRNA molecules. In other embodiments, the template is a cDNA molecule of a population of cDNA molecules. A cDNA template can be synthesized in a nucleic acid synthesis reaction by an enzyme having reverse transcriptase activity, or can be provided from an extrinsic source (e.g., a cDNA library).

Primer. A primer is a single stranded nucleic acid that is shorter than a template, and is complementary to a segment of a template. A primer can hybridize to a template to form a primer-template complex (i.e., a primed template) such that a DNAP can synthesize a nucleic acid molecule (i.e., primer extension product) that is complementary to all or a portion of a template.

Primers typically are 12 to 60 nucleotides long (e.g. 18 to 45 nucleotides long), although they may be shorter or longer in length. A primer is designed to be substantially complementary to a cognate template such that it can specifically hybridize to the template to form a primer-template complex that can serve as a substrate for DNAP to make a primer extension product. In some primer-template complexes, the primer and template are exactly complementary such that each nucleotide of a primer is complementary to and interacts with a template nucleotide. Primers can be made by methods well known in the art (e.g. using an ABI DNA Synthesizer from Applied Biosystems or a Biosearch 8600 or 8800 Series Synthesizer from Milligen-Biosearch, Inc.), or can be obtained from a number of commercial vendors.

DNA polymerase (DNAP). A DNA polymerase is an enzyme that can add deoxynucleoside monophosphate molecules to the 3' hydroxy end of a primer in a primer-template complex, and then sequentially to the 3' hydroxy end of a growing primer extension product according to an RNA or DNA template that directs the synthesis of the polynucleotide. For example, a DNA polymerase can synthesise the formation of a DNA molecule complementary to a single-stranded DNA or RNA template by extending a primer in the 5'-to-3' direction. DNAPs include DNA-dependent DNA polymerases and RNA-dependent DNA polymerases. A given DNAP may have more than one polymerase activity. For example, some DNA-dependent DNA polymerases, such as Taq, also exhibit RNA-directed DNAP activity. DNAPs typically add nucleotides that are complementary to the template being used, but DNAPs may add noncomplementary nucleotides (mismatches) during the polymerization or synthesis process. Thus, the synthesized nucleic acid strand may not be completely complementary to the template. DNAPs may also make nucleic acid molecules that are shorter in length than the template used. DNAPs have two preferred substrates: one is the primer-template complex where the primer terminus has a free 3'-hydroxyl group, the other is a deoxynucleotide 5'-triphosphate (dNTP). A phosphodiester bond is formed by nucleophilic attack of the 3'-OH of the primer terminus on the α-phosphate group of the dNTP and elimination of the terminal pyrophosphate. DNAPs can be isolated from organisms as a matter of routine by those skilled in the art, and can be obtained from a number of commercial vendors.

Some DNAPs are thermostable, and are not substantially inactivated at temperatures commonly used in PCR-based nucleic acid synthesis. Such temperatures vary depending upon reaction parameters, including pH, template and primer nucleotide composition, primer length, and salt concentration. Thermostable DNAPs include *Thermus thermophilus* (Tth) DNAP, *Thermus aquaticus* (Taq) DNAP, *Thermotoga neopolitana* (Tne) DNAP, *Thermotoga maritima* (Tma) DNAP, *Thermatoga* strain FjSS3-B.1 DNAP, *Thermococcus litoralis* (Tli or VENT) DNAP, *Pyrococcus furiosus* (Pfu) DNAP, DEEPVENT™ DNAP, *Pyrococcus woosii* (Pwo) DNAP, *Pyrococcus* sp KOD2 (KOD) DNAP, *Bacillus sterothermophilus* (Bst) DNAP, *Bacillus caldophilus* (Bca) DNAP, *Sulfolobus acidocaldarius* (Sac) DNAP, *Thermoplasma acidophilum* (Tac) DNAP, *Thermus flavus* (Tfl/Tub) DNAP, *Thermus ruber* (Tru) DNAP, *Thermus brockianus* (DYNAZYME™) DNAP, *Thermosipho africanus* DNAP, *Thermococcus zilligi* (Tzi) and mutants, variants and derivatives thereof (see e.g., U.S. Pat. No. 6,077,664; U.S. Pat. No. 5,436,149; U.S. Pat. No. 4,889,818; U.S. Pat. No. 5,532,600; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 94/26766; WO 92/06188; WO 92/03556; WO 89/06691; WO 91/09950; 91/09944; WO 92/06200; WO 96/10640; WO 97/09451; PCT WO03/025132; U.S. Provisional Patent Application Ser. No. 60/647,408, filed Jan. 28, 2005; Barnes, W. *Gene* 112:29-35 (1992); Lawyer, F. et al (1993) *PCR Meth. Appl.* 2:275-287; and Flaman, J. et al. (1994) *Nucl. Acids Res.* 22:3259-3260). Other DNAPs are mesophilic, including pol I family DNAPs (e.g., DNAPs from *E. coli, H. influenzae, D. radiodurans, H. pylori, C. aurantiacus, R. Prowazekii, T. pallidum, Synechocysis* sp., *B. subtilis, L. lactis, S. pneumoniae, M. tuberculosis, M. leprae, M. smegmatis*, Bacteriophage L5, phi-C31, T7, T3, T5, SP01, SP02, *S. cerevisiae*, and *D. melanogaster*), pol III type DNAPs, and mutants, variants and derivatives thereof.

RNA-directed DNA polymerases (reverse transcriptases) are enzymes having reverse transcriptase activity (i.e., that catalyze synthesis of DNA from a single-stranded RNA template). Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al. (1988) *Science* 239:487-491; U.S. Pat. Nos. 4,889,818 and 4,965,188), Tne DNA polymerase (WO 96/10640 and WO 97/09451), Tma DNA polymerase (U.S. Pat. No. 5,374,553) and mutants, variants or derivatives thereof (see e.g., WO 97/09451 and WO 98/47912). Some RTs have reduced, substantially reduced or eliminated RNase H activity. By an enzyme "substantially reduced in RNase H activity" is meant that the enzyme has less than about 20%, more preferably less than about 15%, 10% or 5%, and most preferably less than about 2%, of the RNase H activity of the corresponding wild type or RNase H+ enzyme such as wild type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al. (1988) *Nucl. Acids Res.* 16:265 and in Gerard, G. F., et al. (1992) *FOCUS* 14:91. Particularly preferred polypeptides for use in the invention include, but are not limited to, M-MLV H– reverse transcriptase, RSV H– reverse transcriptase, AMV H– reverse transcriptase, RAV (rous-associated virus) H-reverse transcriptase, MAV (myeloblastosis-associated virus) H– reverse transcriptase and HIV H– reverse transcriptase (see U.S. Pat. No. 5,244,797 and WO 98/47912). It will be understood by one of skill in the art that any enzyme capable of producing a DNA molecule from a ribonucleic acid molecule (i.e., having reverse transcriptase activity) may be equivalently used in the compositions, methods and kits of the invention.

Nucleotide. A nucleotide consists of a phosphate group linked by a phosphoester bond to a pentose (ribose in RNA, and deoxyribose in DNA) that is linked in turn to an organic base. The monomeric units of a nucleic acid are nucleotides. Naturally occurring DNA and RNA each contain four different nucleotides: nucleotides having adenine, guanine, cytosine and thymine bases are found in naturally occurring DNA, and nucleotides having adenine, guanine, cytosine and uracil bases found in naturally occurring RNA. The bases adenine, guanine, cytosine, thymine, and uracil often are abbreviated A, G, C, T and U, respectively.

Nucleotides include free mono-, di- and triphosphate forms (i.e., where the phosphate group has one, two or three phosphate moieties, respectively). Thus, nucleotides include ribonucleoside triphosphates (e.g., ATP, UTP, CTG and GTP) and deoxyribonucleoside triphosphates (e.g., dATP, dCTP, dITP, dGTP and dTTP), and derivatives thereof. Nucleotides also include dideoxyribonucleoside triphosphates (ddNTPs, including ddATP, ddCTP, ddGTP, ddITP and ddTTP), and derivatives thereof.

Nucleotide derivatives include [αS]dATP, 7-deaza-dGTP, 7-deaza-dATP, and nucleotide derivatives that confer resistance to nucleolytic degradation. Nucleotide derivatives include nucleotides that are detectably labeled, e.g., with a radioactive isotope such as 32P or 35S, a fluorescent moiety, a chemiluminescent moiety, a bioluminescent moiety or an enzyme.

Primer extension product. A primer extension product is a nucleic acid that includes a primer to which DNAP has added one or more nucleotides. Primer extension products can be as long as, or shorter than the template of a primer-template complex.

Amplifying. Amplifying refers to an in vitro method for increasing the number of copies of a nucleic acid with the use of a DNAP. Nucleic acid amplification results in the addition of nucleotides to a primer or growing primer extension product to form a new molecule complementary to a template. In nucleic acid amplification, a primer extension product and its template can be denatured and used as templates to synthesize additional nucleic acid molecules. An amplification reaction can consist of many rounds of replication (e.g., one PCR may consist of 5 to 100 "cycles" of denaturation and primer extension). General methods for amplifying nucleic acids are well-known to those of skill in the art (see e.g., U.S. Pat. Nos. 4,683,195; 4,683,202; and 4,800,159; Innis, M. A., et al., eds., PCR Protocols: A Guide to Methods and Applications, San Diego, Calif.: Academic Press, Inc. (1990); Griffin, H., and A. Griffin, eds., PCR Technology: Current Innovations, Boca Raton, Fla.: CRC Press (1994)). Amplification methods that can be used in accord with the present invention include PCR (U.S. Pat. Nos. 4,683,195 and 4,683,202), Strand Displacement Amplification (SDA; U.S. Pat. No. 5,455,166; EP 0 684 315), Nucleic Acid Sequenced-Based Amplification (NASBA; U.S. Pat. No. 5,409,818; EP 0 329 822).

Single stranded DNA binding protein (SSB). Single stranded DNA binding proteins (SSBs) are proteins that preferentially bind single stranded DNA (ssDNA) over double-stranded DNA in a nucleotide sequence independent manner. SSBs have been identified in virtually all known organisms, and appear to be important for DNA metabolism, including replication, recombination and repair. Naturally occurring SSBs typically are comprised of two, three or four subunits, which may be the same or different. In general, naturally occurring SSB subunits contains at least one conserved DNA binding domain, or "OB fold" (see e.g., Philipova, D. et al. (1996) *Genes Dev.* 10:2222-2233; and Murzin, A. (1993) *EMBO J.* 12:861-867), such that naturally occurring SSBs have four or more OB folds.

Thermostable SSBs bind ssDNA at 70° C. at least 70% (e.g., at least 80%, at least 85%, at least 90% and at least 95%) as well as they do at 37° C., and are better suited for PCR applications than are mesophilic SSBs. Thermostable SSBs can be obtained from archaea. Archaea are a group of microbes distinguished from eubacteria through 16S rDNA sequence analysis. Archaea can be subdivided into three groups: crenarchaeota, euryarchaeota and korarchaeota (see e.g., Woese, C. and G. Fox (1977) *PNAS* 74: 5088-5090; Woese, C. et al. (1990) *PNAS* 87: 4576-4579; and Barns, S. et al. (1996) *PNAS* 93:9188-9193). Recently, there have been reports on the identification and characterization of euryarchaeota SSBs, including *Methanococcus jannachii* SSB, *Methanobacterium thermoautrophicum* SSB, and *Archaeoglobus fulgidus* SSB, as well as crenarchaeota SSBs, including *Sulfolobus sulfataricus* SSB and *Aeropyrum pernix* SSB (see e.g., Chedin, F. et al. (1998) *Trends Biochem. Sci.* 23:273-277; Haseltine C. et al. (2002) *Mol. Microbiol.* 43:1505-1515; Kelly, T. et al. (1998) *Proc. Natl. Acad. Sci. USA* 95:14634-14639; Klenk, H. et al. (1997) *Nature* 390: 364-370; Smith, D. et al. (1997) *J. Bacteriol.* 179:7135-55; Wadsworth, R. and M. White (2001) *Nucl. Acids Res.* 29:914-920; and in U.S. Patent Application 60/147,680.

Ordinarily skilled artisans can purify SSBs (including archaea SSBs), make recombinant variants, and can measure SSB activity using routine methods, such as those disclosed in Haseltine C. et al. (2002) *Mol. Microbiol.* 43:1505-1515. A non-comprehensive list of known SSBs, with GenBank Accession numbers, is provided in Table 1. Any of these SSBs, including homologs and variants thereof, may be used in the present invention.

TABLE 1

| gi|18978392 | Replication factor A related protein [*Pyrococcus furiosus* DSM 3638] |
|---|---|
| gi|15679384 | Replication factor A related protein [*Methanothermobacter thermautotrophicus*] [*Methanothermobacter thermautotrophicus* str. Delta H] |
| gi|15679383 | Replication factor A related protein [*Methanothermobacter thermautotrophicus*] [*Methanothermobacter thermautotrophicus* str. Delta H] |
| gi|15669348 | Replication factor A related protein [*Methanococcus jannaschii*] [*Methanocaldococcus jannaschii*] |
| gi|14520503 | Replication factor A related protein [*Pyrococcus abyssi*] |
| gi|2622495 | Replication factor A related protein [*Methanothermobacter thermautotrophicus* str. Delta H] |
| gi|2622494 | Replication factor A related protein [*Methanothermobacter thermautotrophicus* str. Delta H] |
| gi|18894230 | Replication factor A related protein [*Pyrococcus furiosus* DSM 3638] |
| gi|7521609 | Replication factor A related protein PAB2163 - *Pyrococcus abyssi* (strain Orsay) |
| gi|7482812 | Replication factor A related protein - *Methanobacterium thermoautotrophicum* (strain Delta H) |
| gi|7482811 | Replication factor A related protein - *Methanobacterium thermoautotrophicum* (strain Delta H) |
| gi|5457718 | Replication factor A related protein [*Pyrococcus abyssi*] |
| gi|1500014 | Replication factor A related protein [*Methanococcus jannaschii*] [*Methanocaldococcus jannaschii*] |
| gi|22299033 | Single-stranded DNA-binding protein [*Thermosynechococcus elongatus* BP-1] |
| gi|17545141 | Single-strand Binding Protein (Helix Destabilizing Protein) [*Ralstonia solanacearum*] |
| gi|15807618 | Single-stranded DNA-binding protein [*Deinococcus radiodurans*] |
| gi|15645859 | Single-strand DNA-binding protein (ssb) [*Helicobacter pylori* 26695] |
| gi|15616611 | Single-strand DNA-binding protein (phage-related protein) [*Bacillus halodurans*] |
| gi|21233884 | Single-strand DNA binding protein [*Proteus vulgaris*] |
| gi|21233779 | Single-strand DNA binding protein [*Proteus vulgaris*] |
| gi|21233694 | Single-strand DNA binding protein [*Proteus vulgaris*] |
| gi|21203068 | Single-strand DNA binding protein [*Proteus vulgaris*] |
| gi|21202963 | Single-strand DNA binding protein [*Proteus vulgaris*] |
| gi|21202878 | Single-strand DNA binding protein [*Proteus vulgaris*] |
| gi|16767506 | ssDNA-binding protein controls activity of RecBCD nuclease [*Salmonella typhimurium* LT2] |
| gi|19746763 | Single strand binding protein [*Streptococcus pyogenes* MGAS8232] |
| gi|19746681 | Single strand binding protein [*Streptococcus pyogenes* MGAS8232] |
| gi|19745475 | Single strand binding protein [*Streptococcus pyogenes* MGAS8232] |
| gi|19745296 | Single strand binding protein [*Streptococcus pyogenes* MGAS8232] |
| gi|22295215 | Single-stranded DNA-binding protein [*Thermosynechococcus elongatus* BP-1] |
| gi|21325755 | Single-stranded DNA-binding protein [*Corynebacterium glutamicum* ATCC 13032] |
| gi|21324632 | Single-stranded DNA-binding protein [*Corynebacterium glutamicum* ATCC 13032] |
| gi|205544 | Single-stranded DNA binding protein precursor [*Rattus* sp.] |
| gi|22124496 | ssDNA-binding protein [*Yersinia pestis* KIM] |
| gi|586039 | Single-strand binding protein (SSB) (Helix-destabilizing protein) |
| gi|417811 | Single-stranded DNA-binding protein, mitochondrial precursor (Mt-SSB) (MtSSB) (PWP1-interacting protein 17) |
| gi|17137188 | Clp-P1; Single stranded-binding protein c6a [*Drosophila melanogaster*] |
| gi|17137156 | Ssb-c31a-P1 [*Drosophila melanogaster*] |
| gi|16422814 | ssDNA-binding protein [*Salmonella typhimurium* LT2] |
| gi|21957289 | ssDNA-binding protein [*Yersinia pestis* KIM] |
| gi|18249854 | Single-stranded DNA binding protein [*Aster yellows phytoplasma*] |
| gi|17981729 | Mitochondrial single stranded DNA-binding protein; low power [*Drosophila melanogaster*] |
| gi|10955315 | Single-strand binding protein [*Escherichia coli*] |
| gi|9507481 | Single-stranded DNA binding protein [Plasmid ColIb-P9] |
| gi|21911117 | Single strand DNA binding protein [*Streptococcus pyogenes* MGAS315] |
| gi|21905327 | Single strand DNA binding protein [*Streptococcus pyogenes* MGAS315] |
| gi|21885285 | Single-stranded DNA binding protein [*Vibrio cholerae*] |
| gi|16751957 | Single-stranded DNA binding protein [Plasmid pIPO2T] |
| gi|16610025 | Single-stranded DNA binding protein [Plasmid pIPO2T] |
| gi|6968505 | Single-strand DNA binding protein [*Campylobacter jejuni* subsp. *jejuni* NCTC 11168] |
| gi|18146307 | Phage-related single-strand DNA-binding protein [*Clostridium perfringens* str. 13] |
| gi|18143945 | Phage-related single-strand DNA-binding protein [*Clostridium perfringens* str. 13] |
| gi|9626285 | Single-stranded DNA binding protein [*Bacteriophage lambda*] |
| gi|21686516 | Single-stranded DNA-binding protein [*Arthrobacter aurescens*] |
| gi|21672790 | Single-strand binding protein [*Buchnera aphidicola* str. Sg (*Schizaphis graminum*)] |
| gi|21203507 | Single-strand DNA-binding protein of phage phi Sa 2 mw [*Staphylococcus aureus* subsp. *aureus* MW2] |

TABLE 1-continued

| | |
|---|---|
| gi\|13700280 | Single-strand DNA-binding protein of phage phi PVL [*Staphylococcus aureus* subsp. *aureus* N315] |
| gi\|21628947 | Single-strand DNA binding (helix-destabilizing) protein [*Haemophilus influenzae* biotype *aegyptius*] |
| gi\|21623439 | Single-strand binding protein [*Buchnera aphidicola* str. Sg (*Schizaphis graminum*)] |
| gi\|21243632 | Single-stranded DNA binding protein [*Xanthomonas axonopodis* pv. *citri* str. 306] |
| gi\|21242946 | Single-stranded DNA binding protein [*Xanthomonas axonopodis* pv. *citri* str. 306] |
| gi\|20809109 | Single-stranded DNA-binding protein [*Thermoanaerobacter tengcongensis*] |
| gi\|20808452 | Single-stranded DNA-binding protein [*Thermoanaerobacter tengcongensis*] |
| gi\|20807311 | Single-stranded DNA-binding protein [*Thermoanaerobacter tengcongensis*] |
| gi\|21591574 | Single-strand DNA binding (helix-destabilizing) protein [*Haemophilus influenzae* biotype *aegyptius*] |
| gi\|17935411 | Single-strand DNA binding protein [*Agrobacterium tumefaciens* str. C58] |
| gi\|16272208 | Single-stranded DNA binding protein (ssb) [*Haemophilus influenzae* Rd] |
| gi\|16131885 | ssDNA-binding protein [*Escherichia coli* K12] |
| gi\|15834295 | ssDNA-binding protein [*Escherichia coli* O157:H7] |
| gi\|15804651 | ssDNA-binding protein [*Escherichia coli* O157:H7 EDL933] |
| gi\|18311623 | Phage-related single-strand DNA-binding protein [*Clostridium perfringens*] |
| gi\|18309269 | Phage-related single-strand DNA binding protein [*Clostridium perfringens*] |
| gi\|16802093 | Single-strand binding protein (SSB) [*Listeria monocytogenes* EGD-e] |
| gi\|16799117 | Single-strand binding protein (SSB) [*Listeria innocua*] |
| gi\|16763010 | Single strand binding protein [*Salmonella enterica* subsp. *enterica* serovar Typhi] |
| gi\|16762936 | Single-strand DNA-binding protein [*Salmonella enterica* subsp. *enterica* serovar Typhi] |
| gi\|16332050 | Single-stranded DNA-binding protein [*Synechocystis* sp. PCC 6803] |
| gi\|16120662 | Single-strand binding protein [*Yersinia pestis*] |
| gi\|16081142 | Single-strand DNA-binding protein [*Bacillus subtilis*] |
| gi\|15965311 | Single-strand binding protein [*Sinorhizobium meliloti*] |
| gi\|15926067 | Single-strand DNA-binding protein of phage phi PVL [*Staphylococcus aureus* subsp. *aureus* N315] |
| gi\|15923356 | Single-strand DNA-binding protein of phage phi PVL [*Staphylococcus aureus* subsp. *aureus* Mu50] |
| gi\|15899120 | Single-stranded DNA binding protein (SSB) [*Sulfolobus solfataricus*] |
| gi\|15896954 | Single strand DNA binding protein, SSB [*Clostridium acetobutylicum*] |
| gi\|15895648 | Single-strand DNA-binding protein, ssb [*Clostridium acetobutylicum*] |
| gi\|15895193 | Phage related SSB-like protein [*Clostridium acetobutylicum*] |
| gi\|15894232 | Single-stranded DNA-binding protein [*Clostridium acetobutylicum*] |
| gi\|15893218 | Single-strand binding protein [*Rickettsia conorii*] |
| gi\|15835919 | SS DNA binding protein [*Chlamydophila pneumoniae* J138] |
| gi\|15829081 | Single-strand DNA binding protein (SSB) (Helix destabilizing protein) [*Mycoplasma pulmonis*] |
| gi\|15828449 | Single strand binding protein [*Mycobacterium leprae*] |
| gi\|15794566 | Single-strand binding protein [*Neisseria meningitidis* Z2491] |
| gi\|15792396 | Single-strand binding protein [*Campylobacter jejuni*] |
| gi\|15618301 | SS DNA Binding Protein [*Chlamydophila pneumoniae* CWL029] |
| gi\|15617138 | Single-strand binding protein [*Buchnera* sp. APS] |
| gi\|15612231 | Single-strand binding protein [*Helicobacter pylori* J99] |
| gi\|15607196 | ssb [*Mycobacterium tuberculosis* H37Rv] |
| gi\|15605660 | Single stranded DNA-binding protein [*Aquifex aeolicus*] |
| gi\|15604763 | SS DNA Binding Protein [*Chlamydia trachomatis*] |
| gi\|15604667 | Single-strand binding protein (ssb) [*Rickettsia prowazekii*] |
| gi\|15603815 | Ssb [*Pasteurella multocida*] |
| gi\|15599428 | Single-stranded DNA-binding protein [*Pseudomonas aeruginosa*] |
| gi\|13507968 | Single-stranded DNA binding protein [*Mycoplasma pneumoniae*] |
| gi\|13358117 | Single-strand binding protein [*Ureaplasma urealyticum*] |
| gi\|12044943 | Single-stranded DNA-binding protein (ssb) [*Mycoplasma genitalium*] |
| gi\|21539818 | Ssb [*Lactococcus lactis* subsp. *cremoris*] |
| gi\|15639056 | Single-strand DNA binding protein (ssb) [*Treponema pallidum*] |
| gi\|15594460 | Single-stranded DNA-binding protein (ssb) [*Borrelia burgdorferi*] |
| gi\|17865707 | Single-strand binding protein (SSB) (Helix-destabilizing protein) |
| gi\|8478517 | Single-strand binding protein (SSB) (Helix-destabilizing protein) |
| gi\|1174443 | Single-strand binding protein (SSB) (Helix-destabilizing protein) |
| gi\|417647 | Single-stranded DNA-binding protein RIM1, mitochondrial precursor (ssDNA-binding protein, mitochondrial) |
| gi\|138390 | Single-stranded DNA binding protein (Helix-destabilizing protein) (Gp32) |
| gi\|134913 | Single-strand binding protein (SSB) (Helix-destabilizing protein) |
| gi\|21400036 | SSB, Single-strand binding protein family [*Bacillus anthracis* A2012] [*Bacillus anthracis* str. A2012] |
| gi\|21397955 | SSB, Single-strand binding protein family [*Bacillus anthracis* A2012] [*Bacillus anthracis* str. A2012] |
| gi\|18920500 | ssb [*Staphylococcus aureus* phage phi 11] |
| gi\|16505317 | Single strand binding protein [*Salmonella enterica* subsp. *enterica* serovar Typhi] |
| gi\|16505243 | Single-strand DNA-binding protein [*Salmonella enterica* subsp. *enterica* serovar Typhi] |
| gi\|16412459 | Single-strand binding protein (SSB) [*Listeria innocua*] |

TABLE 1-continued

| | |
|---|---|
| gi\|16409404 | Single-strand binding protein (SSB) [*Listeria monocytogenes*] |
| gi\|15978425 | Single-strand binding protein [*Yersinia pestis*] |
| gi\|21232166 | Single-stranded DNA binding protein [*Xanthomonas campestris* pv. *campestris* str. ATCC 33913] |
| gi\|21282071 | Single-strand DNA-binding protein of phage phi Sa 2mw [*Staphylococcus aureus* subsp. *aureus* MW2] |
| gi\|21222314 | Single-strand DNA-binding protein [*Streptomyces coelicolor* A3(2)] |
| gi\|21221138 | Single-strand DNA-binding protein [*Streptomyces coelicolor* A3(2)] |
| gi\|21109208 | Single-stranded DNA binding protein [*Xanthomonas axonopodis* pv. *citri* str. 306] |
| gi\|21108448 | Single-stranded DNA binding protein [*Xanthomonas axonopodis* pv. *citri* str. 306] |
| gi\|8978758 | SS DNA binding protein [*Chlamydophila pneumoniae* J138] |
| gi\|21113919 | Single-stranded DNA binding protein [*Xanthomonas campestris* pv. *campestris* str. ATCC 33913] |
| gi\|20910891 | Single-stranded DNA binding protein, mitochondrial precursor (MT-SSB) (MTSSB) (P16) [*Mus musculus*] |
| gi\|8052392 | Single-strand DNA-binding protein [*Streptomyces coelicolor* A3(2)] |
| gi\|4808403 | Single-strand DNA-binding protein [*Streptomyces coelicolor* A3(2)] |
| gi\|20517787 | Single-stranded DNA-binding protein [*Thermoanaerobacter tengcongensis*] |
| gi\|20517069 | Single-stranded DNA-binding protein [*Thermoanaerobacter tengcongensis*] |
| gi\|20515823 | Single-stranded DNA-binding protein [*Thermoanaerobacter tengcongensis*] |
| gi\|15074901 | SSB protein [*Streptococcus pneumoniae* bacteriophage MM1] |
| gi\|19748994 | Single strand binding protein [*Streptococcus pyogenes* MGAS8232] |
| gi\|19748904 | Single strand binding protein [*Streptococcus pyogenes* MGAS8232] |
| gi\|19747591 | Single strand binding protein [*Streptococcus pyogenes* MGAS8232] |
| gi\|19747395 | Single strand binding protein [*Streptococcus pyogenes* MGAS8232] |
| gi\|6647829 | Single-strand binding protein (SSB) (Helix-destabilizing protein) |
| gi\|13432209 | Single-strand binding protein (SSB) (Helix-destabilizing protein) |
| gi\|1711533 | Single-stranded DNA-binding protein, mitochondrial precursor (Mt-SSB) (MtSSB) |
| gi\|10956609 | Single-strand binding protein homolog Ssb [*Corynebacterium glutamicum*] |
| gi\|19352383 | Ssb protein [uncultured bacterium] |
| gi\|15088755 | SSB protein [*Streptococcus pneumoniae* bacteriophage MM1] |
| gi\|19070050 | Ssb protein [uncultured bacterium] |
| gi\|19032310 | Single-stranded DNA-binding protein [*Anabaena variabilis*] |
| gi\|18920719 | Single-strand binding protein Ssb [*Bartonella bacilliformis*] |
| gi\|11875133 | Single-stranded DNA binding protein [*Escherichia coli* O157:H7] |
| gi\|8918883 | Single-strand DNA binding protein [Plasmid F] |
| gi\|7649839 | Ea10 protein; Ssb [*Escherichia coli* O157:H7] |
| gi\|5103190 | Single strand DNA binding protein [Plasmid R100] |
| gi\|15919964 | Ssb protein [Plasmid pSB102] |
| gi\|15722263 | Ssb protein [Plasmid pSB102] |
| gi\|18654211 | Single strand binding protein [Bacteriophage LL-H] |
| gi\|14246134 | Single-strand DNA-binding protein of phage phi PVL [*Staphylococcus aureus* subsp. *aureus* Mu50] |
| gi\|14195223 | Single-strand binding protein (SSB) (Helix-destabilizing protein) |
| gi\|11387162 | Single-strand binding protein (SSB) (Helix-destabilizing protein) |
| gi\|6647831 | Single-strand binding protein (SSB) (Helix-destabilizing protein) |
| gi\|11387134 | Single-strand binding protein (SSB) (Helix-destabilizing protein) |
| gi\|6647828 | Single-strand binding protein (SSB) (Helix-destabilizing protein) |
| gi\|6647827 | Single-strand binding protein (SSB) (Helix-destabilizing protein) |
| gi\|6647825 | Single-strand binding protein (SSB) (Helix-destabilizing protein) |
| gi\|6647824 | Single-strand binding protein (SSB) (Helix-destabilizing protein) |
| gi\|6647823 | Single-strand binding protein (SSB) (Helix-destabilizing protein) |
| gi\|6647820 | Single-strand binding protein (SSB) (Helix-destabilizing protein) |
| gi\|6647819 | Single-strand binding protein (SSB) (Helix-destabilizing protein) |
| gi\|2500889 | Single-stranded DNA binding protein |
| gi\|1351118 | Single-stranded DNA binding protein |
| gi\|730833 | Single-stranded DNA binding protein (SSB) (Helix-destabilizing protein) |
| gi\|134905 | Single-stranded DNA binding protein (SSB) (Helix-destabilizing protein) |
| gi\|4507231 | Single-stranded DNA-binding protein 1 [*Homo sapiens*] |
| gi\|14794570 | Ssb [Cloning vector pRK310] |
| gi\|18150888 | SSB protein [*Pseudomonas putida*] |
| gi\|18143627 | Single-stranded DNA binding protein [*Aster yellows phytoplasma*] |
| gi\|18104278 | ssb protein [*Enterococcus faecalis*] |
| gi\|18104262 | ssb protein [*Enterococcus faecalis*] |
| gi\|18077129 | SSB protein [*Pseudomonas putida*] |
| gi\|17977995 | Single stranded DNA-binding protein SSB [*Escherichia coli*] |
| gi\|17864928 | SSB-like protein [*Haemophilus influenzae* biotype *aegyptius*] |
| gi\|17739937 | Single-strand DNA binding protein [*Agrobacterium tumefaciens* str. C58] |
| gi\|9507773 | Single-strand DNA binding protein [Plasmid F] |
| gi\|9507591 | Single strand DNA binding protein [Plasmid R100] |
| gi\|17427432 | Single-strand binding protein (helix destabilizing protein) [*Ralstonia solanacearum*] |
| gi\|17381298 | SSB protein [uncultured bacterium] |
| gi\|13561952 | Single-stranded DNA-binding protein [*Mycobacterium smegmatis*] |
| gi\|12830947 | SSB [bacteriophage bIL286] |
| gi\|12830884 | SSB protein [bacteriophage bIL285] |
| gi\|5001700 | Single-strand binding protein; SSB [Bacteriophage Tuc2009] |

TABLE 1-continued

| | |
|---|---|
| gi\|82212 | ssb protein homolog - common tobacco chloroplast |
| gi\|13786543 | SSB [*Lactococcus lactis* bacteriophage TP901-1] |
| gi\|13661686 | SSB [*Lactococcus lactis* bacteriophage TP901-1] |
| gi\|13095695 | SSB protein [bacteriophage bIL285] |
| gi\|12829834 | Single stranded binding protein [*Lactococcus lactis* bacteriophage TP901-1] |
| gi\|12248112 | SSB [*Bacillus* phage GA-1] |
| gi\|9632484 | Single-stranded DNA binding protein [Bacteriophage 933W] |
| gi\|16973267 | ssb protein [uncultured bacterium] |
| gi\|16798847 | SSB protein [Bacteriophage A118] |
| gi\|13487814 | Single-strand binding protein; SSB [Bacteriophage Tuc2009] |
| gi\|13095758 | SSB [bacteriophage bIL286] |
| gi\|12141282 | SSB [*Bacillus* phage GA-1] |
| gi\|7960759 | Single-stranded DNA binding protein [*Bacillus* phage Nf] |
| gi\|6094357 | Single-strand binding protein (SSB) (EARLY PROTEIN GP5) |
| gi\|6094356 | Single-strand binding protein (SSB) (EARLY PROTEIN GP5) |
| gi\|5823662 | SSB protein [Bacteriophage A118] |
| gi\|5354247 | ssb; helix-destabilizing [Enterobacteria phage T4] |
| gi\|4426959 | Single-stranded DNA-binding protein SSB-P1 [Enterobacteria phage P1] |
| gi\|4262664 | SSB [Bacteriophage TuIb] |
| gi\|4262663 | SSB [Bacteriophage Mi] |
| gi\|3915274 | Single-stranded DNA binding protein (helix destabilizing protein) (GP32) |
| gi\|3915273 | Single-stranded DNA binding protein (helix destabilizing protein) (GP32) |
| gi\|3915272 | Single-stranded DNA binding protein (helix destabilizing protein) (GP32) |
| gi\|3915271 | Single-stranded DNA binding protein (helix destabilizing protein) (GP32) |
| gi\|3915270 | Single-stranded DNA binding protein (helix destabilizing protein) (GP32) |
| gi\|3915269 | Single-stranded DNA binding protein (helix destabilizing protein) (GP32) |
| gi\|3915268 | Single-stranded DNA binding protein (helix destabilizing protein) (GP32) |
| gi\|3915267 | Single-stranded DNA binding protein (helix destabilizing protein) (GP32) |
| gi\|3915266 | Single-stranded DNA binding protein (helix destabilizing protein) (GP32) |
| gi\|3915265 | Single-stranded DNA binding protein (helix destabilizing protein) (GP32) |
| gi\|3915264 | Single-stranded DNA binding protein (helix destabilizing protein) (GP32) |
| gi\|3915263 | Single-stranded DNA binding protein (helix destabilizing protein) (GP32) |
| gi\|3915262 | Single-stranded DNA binding protein (helix destabilizing protein) (GP32) |
| gi\|3915261 | Single-stranded DNA binding protein (helix destabilizing protein) (GP32) |
| gi\|3915248 | Single-stranded DNA binding protein (helix destabilizing protein) (GP32) |
| gi\|3915242 | Single-stranded DNA binding protein (helix destabilizing protein) (GP32) |
| gi\|2645797 | SSB [Bacteriophage SV76] |
| gi\|2645795 | SSB [Bacteriophage RB69] |
| gi\|2645793 | SSB [Bacteriophage RB32] |
| gi\|2645791 | SSB [Bacteriophage RB27] |
| gi\|2645789 | SSB [Bacteriophage RB18] |
| gi\|2645787 | SSB [Bacteriophage RB15] |
| gi\|2645785 | SSB [Bacteriophage RB10] |
| gi\|2645783 | SSB [Bacteriophage RB9] |
| gi\|2645781 | SSB [Bacteriophage RB8] |
| gi\|2645779 | SSB [Bacteriophage RB6] |
| gi\|2645777 | SSB [Bacteriophage RB3] |
| gi\|2645775 | SSB [Bacteriophage PST] |
| gi\|2645773 | SSB [Bacteriophage M1] |
| gi\|2645770 | SSB [bacteriophage FS-alpha] |
| gi\|2645768 | SSB [Enterobacteria phage SV14] |
| gi\|2645766 | SSB [Bacteriophage RB70] |
| gi\|1429233 | SSB [Bacteriophage B103] |
| gi\|138392 | Helix-destabilizing protein (Single-stranded DNA-binding protein) (SSB protein) |
| gi\|138391 | Single-stranded DNA binding protein (Helix-destabilizing protein) (GP32) |
| gi\|138389 | Helix-destabilizing protein (Single-stranded DNA-binding protein) (SSB protein) |
| gi\|138388 | Single-stranded DNA binding protein (Helix-destabilizing protein) (GP32) |
| gi\|138072 | Single-strand binding protein (SSB) (Early protein GP5) |
| gi\|13937510 | SSB protein [*Pseudomonas* sp. ADP] |
| gi\|15620434 | Single-strand binding protein [*Rickettsia conorii*] |
| gi\|1568593 | ssb [*Mycobacterium tuberculosis* H37Rv] |
| gi\|10955209 | SSB [*Enterobacter aerogenes*] |
| gi\|1572546 | SSB [*Enterobacter aerogenes*] |
| gi\|15026829 | Single-strand DNA-binding protein, SSB [*Clostridium acetobutylicum*] |
| gi\|15025394 | Single-strand DNA-binding protein, ssb [*Clostridium acetobutylicum*] |
| gi\|15024899 | Phage related SSB-like protein [*Clostridium acetobutylicum*] |
| gi\|13815667 | Single-stranded DNA binding protein (SSB) [*Sulfolobus solfataricus*] |
| gi\|9837391 | Ssb [*Flavobacterium johnsoniae*] |
| gi\|14090025 | Single-strand binding protein (SSB) (Helix-destabilizing protein) [*Mycoplasma pulmonis*] |
| gi\|13992542 | Single-stranded DNA binding [*Oryctolagus cuniculus*] |
| gi\|13774090 | Single-stranded DNA binding protein [*Aster yellows phytoplasma*] |
| gi\|13661656 | Single strand binding protein Ssb [*Comamonas testosteroni*] |
| gi\|12519013 | ssDNA-binding protein [*Escherichia coli* O157:H7 EDL933] |
| gi\|13364518 | ssDNA-binding protein [*Escherichia coli* O157:H7] |
| gi\|4115492 | Single strand binding protein [*Phytoplasma* sp.] |
| gi\|12722386 | Ssb [*Pasteurella multocida*] |
| gi\|10954410 | Single strand binding protein [*Actinobacillus actinomycetemcomitans*] |

TABLE 1-continued

| | |
|---|---|
| gi\|10880887 | Single strand binding protein [*Actinobacillus actinomycetemcomitans*] |
| gi\|13093879 | Single strand binding protein [*Mycobacterium leprae*] |
| gi\|4583407 | Single-strand binding protein homolog Ssb [*Corynebacterium glutamicum*] |
| gi\|10176674 | Single-strand DNA-binding protein (phage-related protein) [*Bacillus halodurans*] |
| gi\|7380314 | Single-stranded binding protein [*Neisseria meningitidis* Z2491] |
| gi\|4376665 | SS DNA Binding Protein [*Chlamydophila pneumoniae* CWL029] |
| gi\|1790494 | ssDNA-binding protein [*Escherichia coli* K12] |
| gi\|7428645 | Single-stranded DNA-binding protein 1 precursor, mitochondrial - African clawed frog |
| gi\|1674304 | Single-stranded DNA binding protein [*Mycoplasma pneumoniae*] |
| gi\|7439948 | Single-strand binding protein (ssb) RP836 - *Rickettsia prowazekii* |
| gi\|7439930 | ssb protein - *Mycobacterium tuberculosis* (strain H37RV) |
| gi\|7439921 | Single-stranded DNA-binding protein 2 precursor, mitochondrial - African clawed frog |
| gi\|2146650 | Single-stranded DNA-binding protein ssb - *Mycoplasma pneumoniae* (strain ATCC 29342) |
| gi\|2127217 | Single-stranded DNA-binding protein ssb - *Bacillus subtilis* |
| gi\|2120579 | Single-stranded DNA-binding protein - *Brucella abortus* |
| gi\|2119790 | Excinuclease ABC chain A - *Brucella abortus* (fragment) |
| gi\|423723 | Single-stranded mitochondrial DNA-binding protein precursor - rat |
| gi\|423082 | Single-stranded mitochondrial DNA-binding protein precursor - human |
| gi\|96089 | Helix-destabilizing protein - plasmid RK2 |
| gi\|3328436 | SS DNA Binding Protein [*Chlamydia trachomatis*] |
| gi\|6899559 | Single-stranded binding protein [*Ureaplasma urealyticum*] |
| gi\|7297359 | Ssb-c31a gene product [*Drosophila melanogaster*] |
| gi\|9954966 | Chain D, Crystal Structure Of Chymotryptic Fragment Of *E. Coli* Ssb Bound To Two 35-Mer Single Strand Dnas |
| gi\|9954965 | Chain C, Crystal Structure Of Chymotryptic Fragment Of *E. Coli* Ssb Bound To Two 35-Mer Single Strand Dnas |
| gi\|9954964 | Chain B, Crystal Structure Of Chymotryptic Fragment Of *E. Coli* Ssb Bound To Two 35-Mer Single Strand Dnas |
| gi\|9954963 | Chain A, Crystal Structure Of Chymotryptic Fragment Of *E. Coli* Ssb Bound To Two 35-Mer Single Strand Dnas |
| gi\|10039203 | Single-strand binding protein [*Buchnera* sp. APS] |
| gi\|9950448 | Single-stranded DNA-binding protein [*Pseudomonas aeruginosa*] |
| gi\|9230773 | Single stranded DNA-binding protein [*Thermus aquaticus*] |
| gi\|6841054 | Single-stranded DNA-binding protein [*Borrelia hermsii*] |
| gi\|8569292 | Chain D, Crystal Structure Analysis Of Single Stranded Dna Binding Protein (Ssb) From *E. Coli* |
| gi\|8569291 | Chain C, Crystal Structure Analysis Of Single Stranded Dna Binding Protein (Ssb) From *E. Coli* |
| gi\|8569290 | Chain B, Crystal Structure Analysis Of Single Stranded Dna Binding Protein (Ssb) From *E. Coli* |
| gi\|8569289 | Chain A, Crystal Structure Analysis Of Single Stranded Dna Binding Protein (Ssb) From *E. Coli* |
| gi\|8548923 | Single stranded binding protein [*Thermus thermophilus*] |
| gi\|7388261 | Single-strand binding protein (SSB) (Helix destabilizing protein) |
| gi\|2815500 | Single-strand DNA-binding protein R, mitochondrial precursor (MT-SSB-R) (MT-SSB 2) |
| gi\|586040 | Single-strand binding protein (SSB) (Helix destabilizing protein) |
| gi\|417812 | Single-strand DNA-binding protein, mitochondrial precursor (MT-SSB) (MTSSB) (P16) |
| gi\|134916 | Single-strand binding protein (SSB) (Helix destabilizing protein) |
| gi\|134914 | Single-strand binding protein (SSB) (Helix destabilizing protein) |
| gi\|134912 | Single-strand DNA-binding protein S, mitochondrial precursor (MT-SSB-S) (MT-SSB 1) |
| gi\|134910 | Single-strand binding protein (SSB) (Helix destabilizing protein) |
| gi\|134906 | Single-strand binding protein (SSB) (Helix destabilizing protein) |
| gi\|134904 | Single-strand binding protein (SSB) (Helix destabilizing protein) |
| gi\|134903 | Single-strand binding protein (SSB) (Helix destabilizing protein) |
| gi\|6513859 | Single strand binding protein [*Salmonella typhi*] |
| gi\|7439942 | Single-stranded DNA-binding protein (ssb) homolog - Lyme disease spirochete |
| gi\|7439928 | Single-strand DNA binding protein (ssb) - *syphilis spirochete* |
| gi\|7428646 | Single-stranded DNA-binding protein - *Escherichia coli* |
| gi\|1361850 | Single-stranded DNA binding protein ssb homolog - *Mycoplasma genitalium* |
| gi\|484396 | Single-stranded DNA-binding protein - *Serratia marcescens* |
| gi\|70818 | Single-stranded DNA-binding protein - *Escherichia coli* plasmid F |
| gi\|70817 | Single-stranded DNA-binding protein - *Escherichia coli* plasmid ColIb-P9 |
| gi\|7264824 | Single-stranded DNA-binding protein [*Escherichia coli*] |
| gi\|3114758 | Single strand DNA binding protein [*Campylobacter jejuni*] |
| gi\|6739548 | SSB protein [*Thermus thermophilus*] |
| gi\|466378 | SSB [Plasmid R751] |
| gi\|2735512 | SSB [*Staphylococcus carnosus*] |
| gi\|4688844 | SSB protein [*Escherichia coli*] |
| gi\|6066193 | Single strand binding protein [*Sinorhizobium meliloti*] |
| gi\|6015512 | SSB-like protein [unidentified] |
| gi\|2959411 | Single-stranded binding protein [*Mycobacterium leprae*] |
| gi\|5702178 | Single stranded DNA binding protein [*Escherichia coli*] |

TABLE 1-continued

| | |
|---|---|
| gi\|3337047 | Single-strand binding protein [*Escherichia coli*] |
| gi\|4585395 | Single-stranded DNA binding protein [Bacteriophage 933W] |
| gi\|2314411 | Single-strand DNA-binding protein (ssb) [*Helicobacter pylori* 26695] |
| gi\|4512478 | Single-stranded DNA binding protein [Plasmid ColIb-P9] |
| gi\|4377534 | ssb protein [*Escherichia coli*] |
| gi\|3851548 | Single strand DNA-binding protein; SSB [*Vibrio cholerae*] |
| gi\|4261534 | Single-stranded DNA binding protein [*Saccharomyces cerevisiae*] |
| gi\|4155774 | Single-stranded binding protein [*Helicobacter pylori* J99] |
| gi\|4099056 | Single-stranded DNA binding protein [*Rhodobacter sphaeroides*] |
| gi\|3861362 | Single-strand binding protein (ssb) [*Rickettsia prowazekii*] |
| gi\|3844678 | Single-stranded DNA-binding protein (ssb) [*Mycoplasma genitalium*] |
| gi\|3822198 | Single strand binding protein [*Escherichia coli* O157:H7] |
| gi\|2780888 | Chain D, Structure Of Single Stranded Dna Binding Protein (Ssb) |
| gi\|2780887 | Chain C, Structure Of Single Stranded Dna Binding Protein (Ssb) |
| gi\|2780886 | Chain B, Structure Of Single Stranded Dna Binding Protein (Ssb) |
| gi\|2780885 | Chain A, Structure Of Single Stranded Dna Binding Protein (Ssb) |
| gi\|2687989 | Single-stranded DNA-binding protein (ssb) [*Borrelia burgdorferi*] |
| gi\|3322320 | Single-strand DNA binding protein (ssb) [*Treponema pallidum*] |
| gi\|1502417 | Single-stranded DNA binding protein p12 subunit [*Schizosaccharomyces pombe*] |
| gi\|1502415 | Single-stranded DNA binding protein p30 subunit [*Schizosaccharomyces pombe*] |
| gi\|1502413 | Single-stranded DNA binding protein p68 subunit [*Schizosaccharomyces pombe*] |
| gi\|396394 | Single-strand DNA-binding protein [*Escherichia coli*] |
| gi\|3600051 | Similar to the single-strand binding proteins family (Pfam: SSB.hmm, score: 24.02) [*Arabidopsis thaliana*] |
| gi\|3323586 | Single-strand binding protein [*Salmonella typhimurium*] |
| gi\|1573216 | Single-stranded DNA binding protein (ssb) [*Haemophilus influenzae* Rd] |
| gi\|2982816 | Single stranded DNA-binding protein [*Aquifex aeolicus*] |
| gi\|2636637 | Single-strand DNA-binding protein [*Bacillus subtilis*] |
| gi\|467374 | Single strand DNA binding protein [*Bacillus subtilis*] |
| gi\|104268 | Single-stranded DNA-binding protein r - African clawed frog mitochondrion (SGC1) |
| gi\|104182 | Single-stranded DNA-binding protein 1 precursor, mitochondrial - African clawed frog |
| gi\|1490785 | Single stranded DNA-binding protein [*Shewanella* sp. SC2A] |
| gi\|1490783 | Single stranded DNA-binding protein [*Shewanella* sp. F1A] |
| gi\|1490781 | Single stranded DNA-binding protein [*Shewanella* sp. PT99] |
| gi\|1490779 | Single stranded DNA-binding protein [*Shewanella hanedai*] |
| gi\|483597 | Single-stranded DNA binding protein [*Pseudomonas aeruginosa*] |
| gi\|264475 | SSb = 12 kda basic functional DNA binding region of 30 kda single-stranded nucleic-acid-specific acidic protein {N-terminal} [*Pisum sativum* = peas, cv. Arkel, Peptide Chloroplast Partial, 20 aa] |
| gi\|264474 | SSB = 28 kda single-stranded nucleic-acid-specific acidic protein {N-terminal} [*Pisum sativum* = peas, cv. Arkel, Peptide Chloroplast Partial, 17 aa] |
| gi\|264473 | SSB = 30 kda single-stranded nucleic-acid-specific acidic protein {N-terminal} [*Pisum sativum* = peas, cv. Arkel, Peptide Chloroplast Partial, 25 aa] |
| gi\|264472 | SSB = 33 kda single-stranded nucleic-acid-specific acidic protein {N-terminal} [*Pisum sativum* = peas, cv. Arkel, Peptide Chloroplast Partial, 25 aa] |
| gi\|254074 | Single-stranded DNA binding protein; SSB [*Saccharomyces cerevisiae*] |
| gi\|1097885 | ssDNA-binding protein |
| gi\|225266 | ssb-like ORF 273 |
| gi\|64899 | mitochondrial DNA specific single-stranded DNA binding protein (mt-SSB) [*Xenopus laevis*] |
| gi\|47270 | Single-stranded DNA-binding protein [*Serratia marcescens*] |
| gi\|45638 | Single-stranded DNA-binding protein [*Proteus mirabilis*] |
| gi\|144656 | Single-stranded DNA-binding protein [Plasmid ColIb-P9] |
| gi\|1107472 | Single stranded DNA binding protein [Plasmid F] |
| gi\|662792 | Single-stranded DNA binding protein [uncultured *eubacterium*] |
| gi\|507347 | SSB [*Haemophilus influenzae*] |
| gi\|188856 | Single stranded DNA binding protein [*Homo sapiens*] |
| gi\|552025 | Single stranded DNA binding protein [*Salmonella typhimurium*] |
| gi\|147870 | Single-strand DNA-binding protein (ssb) [*Escherichia coli*] |
| gi\|409951 | Mitochondrial single-stranded DNA-binding protein [*Drosophila melanogaster*] |
| gi\|144126 | Single stranded DNA binding protein [*Brucella melitensis biovar Abortus*] |

Isolated. With respect to polypeptides, "isolated" refers to a polypeptide that constitutes a major component in a mixture of components, e.g., 30% or more, 40% or more, 50% or more, 60% or more, 70% or more, 80% or more, 90% or more, or 95% or more by weight. Isolated polypeptides typically are obtained by purification from an organism that contains the polypeptide (e.g., a transgenic organism that expresses the polypeptide), although chemical synthesis is also feasible.

Methods of polypeptide purification include, for example, ammonium sulfate precipitation, chromatography and immunoaffinity techniques.

A polypeptide of the invention can be detected by any means known in the art, including sodium dodecyl sulfate (SDS)-polyacrylamide gel electrophoresis followed by Coomassie Blue-staining or Western blot analysis using monoclonal or polyclonal antibodies that have binding affinity for the polypeptide to be detected.

Thermostable. "Thermostable" refers to an enzyme or protein (e.g., DNAP, RT and SSB) that is resistant to inactivation by heat. In general, a thermostable enzyme is more resistant to heat inactivation than a mesophilic enzyme. Thus, the nucleic acid synthesis activity or single stranded binding activity of thermostable enzyme or protein may be reduced by heat treatment to some extent, but not as much as mesophilic enzyme or protein.

A thermostable DNAP retains at least 50% (e.g., at least 60%, at least 70%, at least 80%, at least 90%, and at least 95%) of its nucleic acid synthetic activity after being heated in a nucleic acid synthesis mixture at 90° C. for 30 seconds. In contrast, mesophilic DNAPs lose most of their nucleic acid synthetic activity after such heat treatment. Thermostable DNAPs typically also have a higher optimum nucleic acid synthesis temperature than the mesophilic T5 DNAP.

Thermostable SSBs bind ssDNA at 70° C. at least 70% (e.g., at least 80%, at least 85%, at least 90%, and at least 95%) as well as they do at 37° C. The degree to which an SSB binds ssDNA at such temperatures can be determined by measuring intrinsic SSB fluorescence. Intrinsic SSB fluorescence is related to conserved OB fold amino acids, and is quenched upon binding to ssDNA (see e.g., Alani, E. et al. (1992) *J. Mol. Biol.* 227:54-71). A routine protocol for determining SSB-ssDNA binding is described in Kelly, T. et al. (1998) *Proc. Natl. Acad. Sci. USA* 95:14634-14639. Briefly, SSB-ssDNA binding reactions are performed in 2 ml buffer containing 30 mM HEPES (pH 7.8), 100 mM NaCl, 5 mM $MgCl_2$, 0.5% inositol and 1 mM DTT. A fixed amount of SSB is incubated with varying quantities of poly(dT), and fluorescence is measured using an excitation wavelength of about 295 nm and an emission wavelength of about 348 nm.

Fidelity. Fidelity refers to the accuracy of nucleic acid polymerization; the ability of DNAP to discriminate correct from incorrect substrates (e.g., nucleotides) when synthesizing nucleic acid molecules which are complementary to a template. The higher the fidelity, the less the enzyme misincorporates nucleotides in the growing strand during nucleic acid synthesis. Thus, an increase or enhancement in fidelity results in more faithful nucleic acid synthesis by DNAP or RT, with decreased misincorporation.

Increased/enhanced/higher fidelity means having an increase in fidelity, preferably about 1.2 to about 10,000 fold, about 1.5 to about 10,000 fold, about 2 to about 5,000 fold, or about 2 to about 2000 fold (preferably greater than about 5 fold, more preferably greater than about 10 fold, still more preferably greater than about 50 fold, still more preferably greater than about 100 fold, still more preferably greater than about 500 fold and most preferably greater than about 100 fold) reduction in the number of misincorporated nucleotides during synthesis of a nucleic acid of given length compared to the fidelity of a control DNAP (e.g., in the absence of SSBs) during nucleic acid synthesis.

Reduced misincorporation means less than 90%, less than 85%, less than 75%, less than 70%, less than 60%, or preferably less than 50%, preferably less than 25%, more preferably less than 10%, and most preferably less than 1% of relative misincorporation compared to a control DNAP (e.g., in the absence of SSBs) during nucleic acid polymerization.

Homologs and Variants. Homologs and variants suitable for the compositions and methods of the invention can be identified by homologous nucleotide and polypeptide sequence analyses. Known polypeptides in one organism can be used to identify homologous polypeptides in another organism. For example, performing a query on a database of nucleotide or polypeptide sequences can identify homologs of a known polypeptide. Homologous sequence analysis can involve BLAST or PSI-BLAST analysis of databases using known polypeptide amino acid sequences. Those proteins in the database that have greater than 35% sequence identity are candidates for further evaluation for suitability in the compositions and methods of the invention. If desired, manual inspection of such candidates can be carried out in order to narrow the number of candidates that can be further evaluated. Manual inspection is performed by selecting those candidates that appear to have domains conserved among known polypeptides Vector. A vector is a nucleic acid such as a plasmid, cosmid, phage, or phagemid that can replicate autonomously in a host cell. A vector has one or a small number of sites that can be cut by a restriction endonuclease in a determinable fashion, and into which DNA can be inserted. A vector also can include a marker suitable for use in identifying hosts that contain the vector. Markers confer a recognizable phenotype on host cells in which such markers are expressed. Commonly used markers include antibiotic resistance genes such as those that confer tetracycline resistance or ampicillin resistance. Vectors also can contain sequences encoding polypeptides that facilitate the introduction of the vector into a host. Such polypeptides also can facilitate the maintenance of the vector in a host. "Expression vectors" include nucleic acid sequences that can enhance and/or regulate the expression of inserted DNA, after introduction into a host. Expression vectors contain one or more regulatory elements operably linked to a DNA insert. Such regulatory elements include promoter sequences, enhancer sequences, response elements, protein recognition sites, or inducible elements that modulate expression of a nucleic acid. As used herein, "operably linked" refers to positioning of a regulatory element in a vector relative to a DNA insert in such a way as to permit or facilitate transcription of the insert and/or translation of resultant RNA transcripts. The choice of element(s) included in an expression vector depends upon several factors, including, replication efficiency, selectability, inducibility, desired expression level, and cell or tissue specificity.

Host. The term "host" includes prokaryotes, such as *E. coli*, and eukaryotes, such as fungal, insect, plant and animal cells. Animal cells include, for example, COS cells and HeLa cells. Fungal cells include yeast cells, such as *Saccharomyces cereviseae* cells. A host cell can be transformed or transfected with a vector using techniques known to those of ordinary skill in the art, such as calcium phosphate or lithium acetate precipitation, electroporation, lipofection and particle bombardment. Host cells that contain a vector or portion thereof (a.k.a. "recombinant hosts") can be used for such purposes as propagating the vector, producing a nucleic acid (e.g., DNA, RNA, antisense RNA) or expressing a polypeptide. In some cases, a recombinant host contains all or part of a vector (e.g., a DNA insert) on the host genome.

SSB-DNAP Fusion Proteins

An SSB-DNAP fusion protein may be constructed with the SSB portion at the N-terminus and the polymerase portion at the C-terminus or vice-versa. Thus, the DNA construct encoding the fusion protein may comprise the SSB portion upstream (5') of the polymerase portion or vice versa. SSB genes are cloned upstream (or downstream) and in frame with a DNAP gene using methods well known in the art of molecular biology. In one embodiment, the DNAP is a DNA-directed DNA polymerase. In another embodiment, the DNAP is an RNA-directed DNA polymerase. The two portions may be immediately adjacent to each other, or may be separated by an amino acid linker. The amino acid linker may be 1, 2, 3, 4, 5, 6, 7, 8, 9, 10, 11, 12, 13, 14, 15, 16, 17, 18, 19, 20, 25, 30, 40, 50, 60, 70, 80, 90 or 100 or more amino acids in length. In one embodiment, the SSB(s) are thermostable. In some embodiments, nucleic acid synthesis compositions of the invention include two or more fusion proteins. In one embodiment, the SSBs are thermostable SSBs.

SSB-DNAP fusion proteins include, but are not limited to, polypeptides comprising, or consisting of, the amino acid sequence shown in SEQ ID NO: 2, and/or mutants, fragments, and variants thereof. Such fragments include those that retain substantial polymerase, 3'-5' exonuclease activity and/or 5'-3' exonuclease activity (e.g., at least 50%, 60%, 70%, 80%, 85%, 90%, 95% or 99% of the activity of the fusion protein shown in SEQ ID NO: 2). Although the Sso SSB and polymerase portions of the fusion protein shown in SEQ ID NO: 2 contain an amino acid linker separating the two portions, the two portions may also be joined in the absence of such an amino acid linker. The present invention also includes polynucleotides encoding such polypeptides (e.g., SEQ ID NO: 1), and mutants thereof including insertions, deletions and point mutations.

Expression and Purification of Fusion Proteins

To optimize expression of the fusion proteins described herein, inducible or constitutive promoters well known in the art may be used to control expression of a recombinant fusion protein gene in a recombinant host. Similarly, high or low copy number vectors, well known in the art, may be used to achieve appropriate levels of expression. Vectors having an inducible high copy number may also be useful to enhance expression of the fusion proteins in a recombinant host.

Prokaryotic vectors for constructing the plasmid library include plasmids such as those capable of replication in *E. coli*, including, but not limited to, pBR322, pET-26b(+), ColE1, pSC101, pUC vectors (pUC18, pUC19, etc., in *Molecular Cloning, a Laboratory Manual*, Cold Spring Harbor Laboratory Press, Cold Spring Harbor, N.Y., 1989). *Bacillus* plasmids include pC194, pC221, pC217, etc. (Glyczan, in *Molecular Biology Bacilli*, Academic Press, New York, pp 307-329. 1982). Suitable *Streptomyces* plasmids include pIJ101 (Kendall et al., *J. Bacteriol.* 169:4177-4183, 1987). *Pseudomonas* plasmids are reviewed by John et al. (*Rad. Insec. Dis.* 8:693-704, 1986) and Igaki (*Jpn. J. Bacteriol.* 33:729-742, 1978). Broad-host range plasmids or cosmids, such as pCP13 (Darzins et al., *J. Bacteriol.* 159:9-18, 1984) can also be used.

Fusion protein may be cloned in a prokaryotic host such as *E. coli* or other bacterial species including, but not limited to, *Escherichia, Pseudomonas, Salmonella, Serratia*, and *Proteus*. Eukaryotic hosts also can be used for cloning and expression of wild type or mutant polymerases. Such hosts include yeast, fungi, insect and mammalian cells. Expression of the desired DNA polymerase in such eukaryotic cells may involve the use of eukaryotic regulatory regions which include eukaryotic promoters. Cloning and expressing the fusion proteins in eukaryotic cells may be accomplished by well known techniques using well known eukaryotic vector systems.

Hosts can be transformed by routine, well-known techniques. In one embodiment, transformed colonies are plated and screened for the expression of a fusion protein by transferring transformed *E. coli* colonies to nitrocellulose membranes. After the transformed cells are grown on nitrocellulose, the cells are lysed by standard techniques, and the membranes are then treated at 95° C. for 5 minutes to inactivate the endogenous *E. coli* enzyme. Other temperatures may be used to inactivate the host polymerases depending on the host used and the temperature stability of the fusion protein to be cloned. Fusion protein activity is then detected by assaying for the presence of DNA polymerase activity using well known techniques (i.e. Sanger et al., *Gene* 97:119-123, 1991).

Also described herein are host cells that contain or comprise nucleic acid molecules, and vectors that contain or comprise these nucleic acid molecules. Also included are methods for making the polypeptides (e.g., methods for producing polypeptides using these nucleic acid molecules and host cells). In particular embodiments, polypeptides are provided in (1) isolated, (2) substantially pure, and/or (3) essentially pure forms. Other aspects include compositions and mixtures (e.g., reaction mixtures) that contain or comprise one or more polypeptides and/or more polynucleotides described herein.

To optimize expression of the fusion proteins, inducible or constitutive promoters are well known and may be used to express high levels of a fusion protein in a recombinant host. Similarly, high copy number vectors, well known in the art, may be used to achieve or enhance expression of the fusion protein in a recombinant host.

To express the desired fusion protein in a prokaryotic cell (such as, *E. coli, B. subtilis, Pseudomonas*, etc.), the gene encoding the fusion protein may be operably linked to a functional prokaryotic promoter. However, the natural promoter may function in prokaryotic hosts allowing expression of the fusion protein. Thus, the natural promoter or other promoters may be used to express the fusion protein. Such other promoters may be used to enhance expression and may either be constitutive or regulatable (i.e., inducible or derepressible) promoters. Examples of constitutive promoters include the int promoter of bacteriophage λ, and the bla promoter of the β-lactamase gene of pBR322. Examples of inducible prokaryotic promoters include the major right and left promoters of bacteriophage λ, (PR and PL), trp, recA, lacZ, lacI, tet, gal, trc, and tac promoters of *E. coli*. The *B. subtilis* promoters include α-amylase (Ulmanen et al., *J. Bacteriol* 162:176-182 (1985)) and *Bacillus* bacteriophage promoters (Gryczan, T., supra.). *Streptomyces* promoters are described by Ward et al., *Mol. Gen. Genet.* 203:468-478, 1986). Prokaryotic promoters are also reviewed by Glick, *J. Ind. Microbiol.* 1:277-282, 1987; Cenatiempto, Y., *Biochimie* 68:505-516, 1986; and Gottesman, *Ann. Rev. Genet.* 18:415-442 (1984). Expression in a prokaryotic cell also requires the presence of a ribosomal binding site upstream of the gene-encoding sequence. Such ribosomal binding sites are disclosed, for example, by Gold et al., *Ann. Rev. Microbiol.* 35:365-404 (1981).

In one embodiment, the fusion proteins described herein are produced by fermentation of the recombinant host containing and expressing the cloned fusion protein gene. Any nutrient that can be assimilated by the thermophile of interest, or a host containing the cloned fusion protein gene, may be added to the culture medium. Optimal culture conditions should be selected case by case according to the strain used and the composition of the culture medium. Antibiotics may also be added to the growth media to insure maintenance of vector DNA containing the desired gene to be expressed.

Recombinant host cells producing the fusion proteins of the invention can be separated from liquid culture, for example, by centrifugation. In general, the collected microbial cells are dispersed in a suitable buffer, and then broken down by ultrasonic treatment or by other well known procedures to allow extraction of the enzymes by the buffer solution. After removal of cell debris by ultracentrifugation or centrifugation, the fusion protein can be purified by standard protein purification techniques such as extraction, precipitation, chromatography, affinity chromatography, electrophoresis or the like. Assays to detect the presence of the fusion proteins during purification are well known in the art and can be used during conventional biochemical purification methods to determine the presence of these enzymes.

Use of Fusion Proteins The fusion proteins described herein may be used in well known DNA sequencing, DNA labeling, DNA amplification or cDNA synthesis reactions. The fusion proteins may also be used to analyze and/or type polymorphic DNA Fragments Nucleic Acid Synthesis SSB-DNAP fusion proteins may be used in nucleic acid synthesis reactions which comprise: (a) mixing one or more templates with one or more fusion proteins to form a mixture; and (b) incubating the mixture under conditions sufficient to make a nucleic acid complementary to all or a portion of the templates (i.e., a primer extension product). Reaction conditions sufficient to allow nucleic acid synthesis (e.g., pH, temperature, ionic strength, and incubation time) can be optimized according to routine methods known to those skilled in the art and may involve the use of one or more primers, one or more nucleotides, and/or one or more buffers or buffering salts, or any combination thereof.

SSB-DNAP fusion proteins may be used in amplification methods comprising: (a) mixing one or more templates with one or more fusion proteins to form a mixture; and (b) incubating the mixture under conditions sufficient to amplify a nucleic acid complementary to all or a portion of the templates. Such conditions may involve the use of one or more primers, one or more nucleotides, one or more buffers and/or one or more buffering salts, or any combination thereof. Conditions to facilitate nucleic acid synthesis such as pH, ionic strength, temperature and incubation time can be determined as a matter of routine by those skilled in the art.

Following nucleic acid synthesis, nucleic acids can be isolated for further use or characterization. Synthesized nucleic acids can be separated from other nucleic acids and other constituents present in a nucleic acid synthesis reaction by any means known in the art, including gel electrophoresis, capillary electrophoresis, chromatography (e.g., size, affinity and immunochromatography), density gradient centrifugation, and immunoadsorption. Separating nucleic acids by gel electrophoresis provides a rapid and reproducible means of separating nucleic acids, and permits direct, simultaneous comparison of nucleic acids present in the same or different samples. Nucleic acids made by the provided methods can be isolated using routine methods. For example, nucleic acids can be removed from an electrophoresis gel by electroelution or physical excision. Isolated nucleic acids can be inserted into vectors, including expression vectors, suitable for transfecting or transforming prokaryotic or eukaryotic cells.

DNA Sequencing

SSB-DNAP fusion proteins can be used in sequencing reactions (isothermal DNA sequencing and cycle sequencing of DNA). For example, SSB-DNAP fusion proteins can be used for dideoxy-mediated sequencing involves the use of a chain-termination technique which uses a specific polymer for extension by DNA polymerase, a base-specific chain terminator and the use of polyacrylamide gels to separate the newly synthesized chain-terminated DNA molecules by size so that at least a part of the nucleotide sequence of the original DNA molecule can be determined Specifically, a DNA molecule is sequenced by using four separate DNA sequence reactions, each of which contains different base-specific terminators. For example, the first reaction will contain a G-specific terminator, the second reaction will contain a T-specific terminator, the third reaction will contain an A-specific terminator, and a fourth reaction may contain a C-specific terminator. Preferred terminator nucleotides include dideoxyribonucleoside triphosphates (ddNTPs) such as ddATP, ddTTP, ddGTP, ddITP and ddCTP. Analogs of dideoxyribonucleoside triphosphates may also be used and are well known in the art. Detectably labeled nucleotides are typically included in sequencing reactions. Any number of labeled nucleotides can be used in sequencing (or labeling) reactions, including, but not limited to, radioactive isotopes, fluorescent labels, chemiluminescent labels, bioluminescent labels, and enzyme labels.

The fusion proteins may also be used in cycle sequencing reactions. Cycle sequencing often involves the use of fluorescent dyes. In some cycle sequencing protocols, sequencing primers are labeled with fluorescent dye (e.g., using Amersham Bioscience MegaBACE DYEnamic ET Primers, ABI Prism® BigDye™ primer cycle sequencing kit, and Beckman Coulter WellRED fluorescence dye). Sequencing reactions using fluorescent primers offers advantages in accuracy and readable sequence length. However, separate reactions must be prepared for each nucleotide base for which sequence position is to be determined In other cycle sequencing protocols, fluorescent dye is linked to ddNTP as a dye terminator (e.g., using Amersham Bioscience MegaBACE DYEnamic ET Terminator cycle sequencing kit, ABI Prism® BigDye™ Terminator cycle sequencing kit, ABI Prism® dRhodamine Terminator cycle sequencing kit, LI-COR IRDye™ Terminator Mix, and CEQ Dye Terminator Cycle sequencing kit with Beckman Coulter WellRED dyes). Since dye terminators can be labeled with unique fluorescence dye for each base, sequencing can be done in a single reaction.

Thus, nucleic acids may be sequenced by: (a) mixing one or more templates to be sequenced with one or more fusion proteins (and optionally one or more nucleic acid synthesis terminating agents such as ddNTPs) to form a mixture; (b) incubating the mixture under conditions sufficient to synthesize a population of molecules complementary to all or a portion of the template to be sequenced; and (c) separating the population to determine the nucleotide sequence of all or a portion of the template to be sequenced.

Polymerase Chain Reaction (PCR)

Polymerase chain reaction (PCR), a well known DNA amplification technique, is a process by which DNA polymerase and deoxyribonucleoside triphosphates are used to amplify a target DNA template. In such PCR reactions, two primers, one complementary to the 3' termini (or near the 3'-termini) of the first strand of the DNA molecule to be amplified, and a second primer complementary to the 3' termini (or near the 3'-termini) of the second strand of the DNA molecule to be amplified, are hybridized to their respective DNA strands. After hybridization, DNA polymerase, in the presence of deoxyribonucleoside triphosphates, allows the synthesis of a third DNA molecule complementary to the first strand and a fourth DNA molecule complementary to the second strand of the DNA molecule to be amplified. This synthesis results in two double stranded DNA molecules. Such double stranded DNA molecules may then be used as DNA templates for synthesis of additional DNA molecules by providing a DNA polymerase, primers, and deoxyribonucleoside triphosphates. As is well known, the additional synthesis is carried out by "cycling" the original reaction (with excess primers and deoxyribonucleoside triphosphates) allowing multiple denaturing and synthesis steps. Typically, denaturing of double stranded DNA molecules to form single stranded DNA templates is accomplished by high temperatures. The fusion proteins described herein include those which are heat stable, and thus will survive such thermal cycling during DNA amplification reactions. Thus, these fusion proteins are ideally suited for PCR reactions, particularly where high temperatures are used to denature the DNA molecules during amplification. The fusion proteins may be used in all PCR methods known to one of ordinary skill in the art, including end-point PCR, real-time qPCR (U.S. Pat. Nos. 6,569,627; 5,994,056; 5,210,015; 5,487,972; 5,804,375; 5,994,076, the contents of which are incorporated by reference in their entirety), allele specific amplification, linear PCR, one step reverse transcriptase (RT)-PCR, two step RT-PCR, mutagenic PCR, multiplex PCR and the PCR methods described in copending U.S. patent application Ser. No. 09/599,594, the contents of which are incorporated by reference in their entirety.

Preparation of cDNA

The fusion proteins (SSB-reverse transcriptase enzymes) described herein may also be used to prepare cDNA from mRNA templates. See, for example, U.S. Pat. Nos. 5,405,776 and 5,244,797, the disclosures of which are incorporated herein by reference. Thus, the invention also relates to a method of preparing cDNA from mRNA, comprising (a) contacting mRNA with an oligo(dT) primer or other complementary primer to form a hybrid; and (b) contacting the hybrid formed in step (a) with a fusion protein of the invention and the four dNTPs, whereby a cDNA-RNA hybrid is obtained. If the reaction mixture is step (b) further comprises an appropriate oligonucleotide which is complementary to the cDNA being produced, it is also possible to obtain dsDNA following first strand synthesis. Thus, the invention is also directed to a method of preparing dsDNA with the fusion proteins described herein.

Another embodiment features compositions and reactions for nucleic acid synthesis, sequencing or amplification that include the fusion proteins of the invention. These mixtures include one or more fusion proteins, one or more dNTPs (dATP, dTTP, dGTP, dCTP), a nucleic acid template, an oligonucleotide primer, magnesium and buffer salts, and may also include other components (e.g., nonionic detergent). If sequencing reactions are performed, the reaction may also include one or more ddNTPs. The dNTPs or ddNTPs may be unlabeled or labeled with a fluorescent, chemiluminescent, bioluminescent, enzymatic or radioactive label. In some embodiments, compositions comprising one or more fusion proteins are formulated as described in PCT WO98/06736, the entire contents of which are incorporated herein by reference.

In some embodiments, kits are provided (e.g., for use in carrying out the methods described herein). Such kits may include, in addition to one or more fusion proteins, one or more components selected from the group consisting of: one or more host cells (preferably competent to take up nucleic acid molecules), one or more nucleic acids (e.g., nucleic acid templates), one or more nucleotides, one or more nucleic acid primers, one or more vectors, one or more ligases, one or more topoisomerases, and one or more buffers or buffer salts.

Analyzing and Typing Polymorphic DNA Fragments

In one embodiment, the relationship between a first individual and a second individual may be determined by analyzing and typing a particular polymorphic DNA fragment, such as a minisatellite or microsatellite DNA sequence. In such a method, the amplified fragments for each individual are compared to determine similarities or dissimilarities. Such an analysis is accomplished, for example, by comparing the size of the amplified fragments from each individual, or by comparing the sequence of the amplified fragments from each individual. In another aspect of the invention, genetic identity can be determined. Such identity testing is important, for example, in paternity testing, forensic analysis, etc. In this aspect of the invention, a sample containing DNA is analyzed and compared to a sample from one or more individuals. In one such aspect of the invention, one sample of DNA may be derived from a first individual and another sample may be derived from a second individual whose relationship to the first individual is unknown; comparison of these samples from the first and second individuals by the methods of the invention may then facilitate a determination of the genetic identity or relationship between the first and second a individual. In a particularly preferred such aspect, the first DNA sample may be a known sample derived from a known individual and the second DNA sample may be an unknown sample derived, for example, from crime scene material. In an additional aspect of the invention, one sample of DNA may be derived from a first individual and another sample may be derived from a second individual who is related to the first individual; comparison of these samples from the first and second individuals by the methods of the invention may then facilitate a determination of the genetic kinship of the first and second individuals by allowing examination of the Mendelian inheritance, for example, of a polymorphic, minisatellite, microsatellite or STR DNA fragment.

In another aspect of the invention, DNA fragments important as genetic markers for encoding a gene of interest can be identified and isolated. For example, by comparing samples from different sources, DNA fragments which may be important in causing diseases such as infectious diseases (of bacterial, fungal, parasitic or viral etiology), cancers or genetic diseases, can be identified and characterized. In this aspect of the invention a DNA sample from normal cells or tissue is compared to a DNA sample from diseased cells or tissue. Upon comparison according to the invention, one or more unique polymorphic fragments present in one DNA sample and not present in the other DNA sample can be identified and isolated. Identification of such unique polymorphic fragments allows for identification of sequences associated with, or involved in, causing the diseased state.

Gel electrophoresis is typically performed on agarose or polyacrylamide sequencing gels according to standard protocols using gels containing polyacrylamide at concentrations of 3-12% (e.g., 8%), and containing urea at a concentration of about 4-12M (e.g., 8M). Samples are loaded onto the gels, usually with samples containing amplified DNA fragments prepared from different sources of genomic DNA being loaded into adjacent lanes of the gel to facilitate subsequent comparison. Reference markers of known sizes may be used to facilitate the comparison of samples. Following electrophoretic separation, DNA fragments may be visualized and identified by a variety of techniques that are routine to those of ordinary skill in the art, such as autoradiography. One can then examine the autoradiographic films either for differences in polymorphic fragment patterns ("typing") or for the presence of one or more unique bands in one lane of the gel ("identifying"); the presence of a band in one lane (corresponding to a single sample, cell or tissue type) that is not observed in other lanes indicates that the DNA fragment comprising that unique band is source-specific and thus a potential polymorphic DNA fragment.

Nucleic Acid Synthesis Compositions

Nucleic acid synthesis compositions can include one or more SSB-DNA polymerase or SSB-reverse transcriptase fusion proteins, one or more nucleotides, one or more primers, one or more buffers and/or one or more templates. In some embodiments, a nucleic acid synthesis reaction can include mRNA and a fusion protein having reverse transcriptase activity. These compositions can be used to improve the yield and/or homogeneity of primer extension products made during nucleic acid synthesis (e.g., cDNA synthesis, amplification and combined cDNA synthesis/amplification reactions).

Kits

The fusion proteins described herein are suited for the preparation of a kit. Kits comprising these fusion proteins may be used for detectably labeling DNA molecules, DNA sequencing, amplifying DNA molecules or cDNA synthesis by well known techniques, depending on the content of the kit. See U.S. Pat. Nos. 4,962,020, 5,173,411, 4,795,699, 5,498,523, 5,405,776 and 5,244,797, the disclosures of which are hereby incorporated by reference. Such kits may comprise a carrying means being compartmentalized to receive in close confinement one or more container means such as vials, test tubes and the like. Each of such container means comprises components or a mixture of components needed to perform DNA sequencing, DNA labeling, DNA amplification, or cDNA synthesis.

Such kits may include, in addition to one or more fusion proteins, one or more components selected from the group consisting of one or more host cells (preferably competent to take up nucleic acid molecules), one or more nucleic acids (e.g., nucleic acid templates), one or more nucleotides, one or more nucleic acid primers, one or more vectors, one or more ligases, one or more topoisomerases, and one or more buffers or buffer salts.

Kit constituents typically are provided, individually or collectively, in containers (e.g., vials, tubes, ampules, and bottles). Kits typically include packaging material, including instructions describing how the kit can be used for example to synthesize, amplify or sequence nucleic acids. A first container may, for example, comprise a substantially purified sample of each fusion protein. A second container may comprise one or a number of types of nucleotides needed to synthesize a DNA molecule complementary to DNA template. A third container may comprise one or a number of different types of dideoxynucleoside triphosphates. A fourth container may comprise pyrophosphatase. In addition to the above containers, additional containers may be included in the kit which comprise one or a number of DNA primers. A kit used for amplifying DNA will comprise, for example, a first container comprising a substantially pure fusion protein as described herein and one or a number of additional containers which comprise a single type of nucleotide or mixtures of nucleotides. Various primers may or may not be included in a kit for amplifying DNA. The various kit components need not be provided in separate containers, but may also be provided in various combinations in the same container. For example, the fusion protein and nucleotides may be provided in the same container, or the fusion protein and nucleotides may be provided in different containers.

Kits for cDNA synthesis comprise a first container containing a fusion protein, a second container containing the four dNTPs and the third container containing an oligo(dT) primer. See U.S. Pat. Nos. 5,405,776 and 5,244,797, the disclosures of which are incorporated herein by reference. Since the fusion proteins of the present invention are also capable of preparing dsDNA, a fourth container may contain an appropriate primer complementary to the first strand cDNA. Of course, it is also possible to combine one or more of these reagents in a single tube. When desired, the kit of the present invention may also include a container which comprises detectably labeled nucleotides which may be used during the synthesis or sequencing of a DNA molecule. One of a number of labels may be used to detect such nucleotides. Illustrative labels include, but are not limited to, radioactive isotopes, fluorescent labels, chemiluminescent labels, bioluminescent labels and enzyme labels.

Having now generally described the embodiments, the same will be more readily understood through reference to the following examples which are provided by way of illustration, and are not intending to be limiting of the present invention.

EXAMPLES

The invention is further described in the following examples, which do not limit the scope of the inventions described in the claims.

Example 1

Cloning of Sso SSB-Tzi Polymerase Fusion Protein

The Sso SSB gene was cloned upstream and in-frame with the *T. zilligii* (Tzi) DNA polymerase gene in pET26b (Novagen). There is a 6-mer linker (GSSGVD) (amino acids 151-156 of SEQ ID NO: 2) between the Sso SSB region and the Tzi polymerase region. The DNA sequence of the open reading frame (ORF) for Sso SSB-Tzi is shown in SEQ ID NO: 1, and the corresponding amino acid sequence is shown in SEQ ID NO: 2. The fusion protein consists of an Sso portion (amino acids 1-150), a 6-mer amino acid linker (amino acids 151-156) and a Tzi portion (amino acids 157-941).

```
SEQ ID NO: 1:
5'-atggaagaaaagtaggtaatctgaaaccaaatatggaaagcgtaaatgtaaccgtacgagttttggaagc aagcgaagcacgtcaaatccagacaaagaacggtgttcggacaatcagtgaggctattgttggagatgaaacg ggacgagtaaagttaacattatggggaaaacatgcaggtagtatcaaagaaggtcaagtggtaaagattgaaaa cgcgtggaccaccgcttttaagggtcaagtacagttaaatgctggaagcaaaactaagatcgctgaagcttcag aagatggatttccagaatcatctcaaattccagaaaatacaccaacagctcctcagcaaatgcgtggaggagga cgcggattccgcggtgggggacgtcggtatggacgacgtggtggtcgccggcaagaaaacgaagaaggtga agaggagggaagcggagggtcgacatgatcctcgatgctgactacatcaccgaagacggaaagcccgtca taagggtcttcaagaaggaaaagggcgagtttaagatagactacgacagggactttgagccctacatctacgcc ctcctgaaggacgattccgccattgaggacatcaagaagatcaccgccgagaggcacggcaccaccgttaga gttacccgggcggagagggtgaagaagaagttcctcggcaggccggtggaggtctggaagctctacttcacc
```

-continued

```
caccccaggacgttcccgcgatcagggacaaaatcagggagcatccggcggttgttgacatctacgagtacg acataccttcgcgaagcgctacctcatagacaggggcttaatccctatggaggggacgaggagctcaggat gctcgccttcgacatcgagacgctctaccatgagggggaggagtttggcgaggggcctatcctgatgaagct acgccgatgaagaggggcgcgcgttatcacctggaagaatatcgacctcccctacgtggagagcgtttctact gagaaagagatgataaagcgcttcctcaaggtaatccaggagaaggatccggatgtgctcataacctacaacg gcgacaacttcgactttgcttacctcaagaagcgctcagaaacgctcggcgtcaagttcatcctcggaagggac gggagcgaaccgaaaattcagcgcatgggcgaccgctttgcagtggaggtgaaggggagaatacacttcgac ctctacccggttataaggaggactattaacctccccacctcacccctcgagacagtctacgaggcgattttcggg caaccaaaggagaaggtctacgcggaagagatagcgcgggcctgggagagcggggaaggcttggaaagg gtggcccgctattccatggaggacgcaaaggcaacttacgaactcggaaaagagttcttcccgatggaggccc agctctcgcgcctcgtgggccagagcctctgggatgtatcgcgctcgagcacaggaaacttagttgagtggttt ctcctgaggaaggcctacgagaggaacgagctcgcgccaaacaagccggacgagagggagttagcaagga gagcggagagctacgcggtggatatgtcaaagagcccgaaaaggggctgtgggagaacatagtctacctc gattacaaatctctctacccctcgataatcatcacccacaacgtctcccctgataccctcaacagggagggctgta gggagtacgacgtggcacctcaggtgggacaccgcttctgcaaggacttcccgggctttatcccgagcctcctc ggggacttttggaggagaggcagaaggtaaagaagaaaatgaaggccacggtggacccgatagagagga agctcctcgactacaggcaacgcgccatcaagattctggccaacagttattacggctactacggctacgcaaat gcccgctggtactgcagggagtgcgccgagagcgttaccgcctggggcaggcagtatattgaaaccacgatg agggaaatagaggagaaatttggctttaaagtgctttacgcggataccgacggttctttgccacgattcccgga gcggacgccgaaacggtcaaaaagaaggctaaagaattcctgaactacatcaaccccagactgcccggcctg ctcgagctggagtacgagggcttctacaggcgcggcttcttcgtgacgaagaagaagtacgcggttatagacg aggaggacaagataacgacgcgcgggctggaaatagtaaggcgcgactggagcgagatagcgaaggaga cgcaggcgagggttcttgaggcgatactcaagcacggtgacgtcgaagaggcagtaaggattgtcaaggagg tgacggaaaagctgagtaggtacgaggttccaccggagaagctcgtcatctacgagcagataacccgcgacct gagggactacagggccacggggccgcacgtggccgttgcaaaacgcctcgccgcgaggggggataaaaatc cggcccgggacggtcataagctacatagtgctcaaaggcccgggaagggttggggacagggcgataccctc gacgagttcgaccctgcaaagcaccgctatgatgcggaatactacatcgagaaccaggttcttccagcggtgg agaggattctgagggcctttggttaccgcaaagaggacttgaggtatcagaagacgaagcaggccggactgg gggcgtggctaaaaccgaagacataa-3'
```

SEQ ID NO: 2:

```
  1 MMEEKVGNLK PNMESVNVTV RVLEASEARQ IQTKNGVRTI SEAIVGDETG RVKLTLWGKH
                          Sso
             ~~~~~~~~~~~~~~~~~~~~~~~~~~~~~~~~~~~~~~~~~~~~~~~~~~~~~
 61 AGSIKEGQVV KIENAWTTAF KGQVQLNAGS KTKIAEASED GFPESSQIPE NTPTAPQQMR
                 Sso                              Tzi
             ~~~~~~~~~~~~~~~~~~~~~~~~~~~~~~~   ~~~~~~~~~~~~
121 GGGRGFRGGG RRYGRRGGRR QENEEGEEEG    GSGGVD      MILDADYITED
                                    Tzi
             ~~~~~~~~~~~~~~~~~~~~~~~~~~~~~~~~~~~~~~~~~~~~~~~~~~~~~
168 GKPVIRVFKK ENGEEKIDYD RDFEPYIYAL LKDDSAIEDI KKITAERHGT TVRVTRAERV
                                    Tzi
             ~~~~~~~~~~~~~~~~~~~~~~~~~~~~~~~~~~~~~~~~~~~~~~~~~~~~~
228 KKKFLGRPVE VWKLYFTHPQ DVPAIRDKIR EHPAVVDIYE YDIPFAKRYL IDRGLIPMEG
                                    Tzi
             ~~~~~~~~~~~~~~~~~~~~~~~~~~~~~~~~~~~~~~~~~~~~~~~~~~~~~
288 DEELRMLAFD IETLYHEGEE FGEGPILMIS YADEEGARVI TWKNIDLPYV ESVSTEKEMI
```

```
                            -continued
                            Tzi
348 RFLKVIQEK DPDVLITYNG DNFDFAYLKK RSETLGVKFI LGRDGSEPKI QRMGDRFAVE Tzi
408 KGRIHFDLY PVIRRTINLP TYTLETVYEA IFGQPKEKVY AEEIARAWES GEGLERVARY Tzi
468 SMEDAKATYE LGKEFFPMEA QLSRLVGQSL WDVSRSSTGN LVEWFLLRKA YERNELAPNK Tzi
528 PDERELARRA ESYAGGYVKE PEKGLWENIV YLDYKSLYPS IIITHNVSPD TLNREGCREY Tzi
588 DVAPQVGHRF CKDFPGFIPS LLGDLLEERQ KVKKKMKATV DPIERKLLDY RQRAIKILAN Tzi
648 SYYGYYGYAN ARWYCRECAE SVTAWGRQYI ETTMREIEEK FGFKVLYADT DGFFATIPGA Tzi
708 DAETVKKKAK EFLNYINPRL PGLLELEYEG FYRRGFFVTK KKYAVIDEED KITTRGLEIV Tzi
768 RRDWSEIAKE TQARVLEAIL KHGDVEEAVR IVKEVTEKLS RYEVPPEKLV IYEQITRDLR Tzi
828 DYRATGPHVA VAKRLAARGI KIRPGTVISY IVLKGPGRVG DRAIPFDEFD PAKHRYDAEY Tzi
888 YIENQVLPAV ERILRAFGYR KEDLRYQKTK QAGLGAWLKP KT
```

Example 2

Purification of Sso SSB-Tzi Polymerase Fusion Protein pTTQ-SsoTzi fusion protein was expressed in *E. coli* BL21/DE3 cells containing a plasmid expressing two supplemental tRNAs: ArgU (arginine) and IleY (isoleucine). A 150 mL culture of these cells was grown in LB medium supplemented with 0.18% dextrose, 40 ug/mL chloramphenicol and 100 ug/mL ampicillin at 30° C., overnight. This culture was then diluted into six liters of LB medium and the cells were grown at 37° C. to an OD600 of ~0.8-1.0 and then induced with 1 mM IPTG. The cells continued to grow for 3 hours post-induction and were then harvested by centrifugation at 6,000×g for 20 minutes.

After centrifugation, the cell pellet was resuspended in 3 ml of lysis buffer (50 mM Tris-HCl, pH 7.5, 1 mM EDTA, 8% glycerol, 10 mM KCl, 5 mM b-mercaptoethanol, 50 mg/ml phenylmethylsulfonyl fluoride) per gram of wet cell paste and lysed by sonication (70-80% lysis based on OD600). The lysate was then heat-treated for 30 minutes at 85° C., then immediately placed on ice and sodium chloride (NaCl) was added to a final concentration of 250 mM. Polyethylenimine (PEI; 2% v/v) was added dropwise to the lysate at 4° C. to a final concentration of 0.15% (v/v) and allowed to mix for 30 minutes at 4° C. The lysate was centrifuged for 1 hour in an SS-34 rotor at 17,500 rpm, and the supernatant was retained. A solid ammonium sulfate cut was performed on the supernatant to about 55% saturation while mixing at 4° C. The lysate was centrifuged for 30 min in a SS-34 rotor at 13,000 rpm, and the pellet was resuspended in low salt buffer (30 mM Tris-HCl, pH 7.5, 1 mM EDTA, 1 mM DTT, 10% glycerol, 50 mM NaCl) and dialyzed against low salt buffer overnight.

The solution was applied to a 5 ml EMD-SO4 column (1.6×5 cm) (EM Science) and equilibrated with the low salt buffer. The column was washed with 4 column volumes (cV) of low salt buffer and the protein was eluted with a 15 cV gradient from low salt buffer to 70% of high salt buffer (30 mM Tris HCl, pH 7.5, 1 mM EDTA, 1 mM DTT, 10% glycerol, 1,000 mM NaCl), followed by three cV wash at 70% high salt buffer. Two ml fractions were collected and analyzed by sodium dodecyl sulfate polyacrylamide gel electrophoresis (SDS-PAGE) on 4-20% Tris-glycine gels (Novex) stained with Novex SimplySafe stain according to the manufacturer's instructions. Fractions containing the desired protein band were further analyzed by the Polymerase unit activity assay as follows.

DNA polymerase activity of the Sso SSB-Tzi polymerase fusion protein was assessed by the incorporation rate of radiolabeled nucleotides into a nicked salmon testes DNA template. In this assay, one polymerase unit corresponds to the incorporation of 10 nmol of deoxynucleotides into acid-precipitable material in 30 min. at 74° C. under standard buffer conditions. The nucleotide incorporation into acid-insoluble fractions was measured by spotting an aliquot of the reaction onto a GF/C filter, washing the filter with trichloroacetic acid (TCA) solution, and counting the amount of radioactivity on the filter using a scintillation counter.

For a standard unit assay, 5 µl of a dilution of Sso SSB-Tzi polymerase fusion protein was added to a set of 50 µl reactions. Each reaction contained 0.5 µg/µl of nicked salmon testes DNA and 0.2 mM of each dNTP (dATP, dCTP, dGTP, dTTP) in 1× unit assay buffer (25 mM TAPS, pH 9.3, 50 mM KCl, 2 mM MgCl$_2$, 1 mM DTT and 1 to 2 µCi [α-$^{32}$P] dCTP in a final volume of 50 µl per reaction.

The reaction was initiated upon addition of the fusion protein and transfer to a heating block equilibrated to 74° C. The reaction was continued for 10 min and terminated by adding 10 µl of 0.5 M EDTA to each of the 50 l reactions on ice. 40 µl each of the mixtures was spotted onto a GF/C filter for TCA precipitation. Reactions included a non-saturating amount of polymerase (i.e., in the range where activity linearly corresponds to the dilution factor).

TCA precipitation was performed as follows. The filters were washed in 10% TCA solution containing 1% sodium pyrophosphate for 15 min, in 5% TCA for 10 min three times, then in 95% ethanol for 10 min. The filters were dried under a heat lamp for 5 to 10 min and the radioactivity decay rate was measured in ScintiSafe Econo 1 scintillation cocktail (Fisher Scientific, part # SX20-5) using a Beckman scintillation counter (Model # LS 3801).

Fractions containing optimal polymerase activity were pooled and dialyzed against 2 liters of Resource Q low salt buffer (25 mM Tris-HCl, pH 8, 1 mM EDTA, 1 mM DTT, 10% glycerol, 50 mM NaCl).

The sample was applied to an 8 ml Source Q column (GE Healthcare, Amersham) equilibrated with Source Q low salt buffer (25 mM Tris-HCl, pH 8, 50 mM NaCl, 1 mM EDTA, 10% glycerol). The column was washed with 5 cV of low salt buffer and eluted with 20 cV of a linear gradient from low salt buffer to 50% of high salt buffer (25 mM Tris-HCl, pH 8, 1 mM EDTA, 1 mM DTT, 10% glycerol, 1,000 mM NaCl), followed by an additional three cV wash at 50% of high salt buffer. Two ml fractions were collected and analyzed by sodium dodecyl sulfate polyacrylamide gel electrophoresis (SDS-PAGE) on 4-20% Tris-glycine gels (Novex) stained with Novex SimplySafe stain according to the manufacturer's instructions. Fractions containing the desired protein band were further analyzed by the polymerase unit activity assay. Fractions containing optimal polymerase activity were pooled and dialyzed against 2 liters of storage buffer (20 mM Tris-HCl, pH 8, 40 mM KCl, 0.1 mM EDTA, 1 mM DTT, 50% glycerol). The protein concentration was measured by UV absorbance as described below prior to addition of BigChap and Chapso since these detergents interfere with UV absorbance measurements. BigChap and Chapso were added to final concentrations of 1.2% and 0.12%, respectively. The resulting Sso-Tzi fusion protein was greater than 95% pure.

Example 3

UV Absorbance for Quantitation of Sso SSB-Tzi Polymerase Fusion Protein

The protein concentration determination for Sso SSB-Tzi polymerase fusion protein was performed by UV absorbance at 278 nm. The UV spectrum was measured using a Beckman Model DU-640 spectrophotometer in a Beckman micro quartz cell (8 mm) from 220 to 320 nm. The UV measurement was done in the absence of the detergents, BigChap and Chapso since these interfere with the measurements (see above). Absorbance at 320, 315, 278 and 260 nm were read from the spectrum. The absorbance at 320 and 315 nm were used to calculate slope of the baseline, while the absorbance at 278 and 260 nm were used to estimate the extent of nucleic acid contamination. Absorbance at 278 nm was calibrated by subtracting baseline, calculated from the slope of the baseline, using the equation:

$$\text{Abs}(278)_{cal} = \text{Abs}(278)_{obs} - 8.4 \times (\text{Abs}(315)_{obs} - \text{Abs}(320)_{obs})$$

where $\text{Abs}(278)_{cal}$ is calibrated absorbance at 278 nm, and $\text{Abs}(278)_{obs}$, $\text{Abs}(310)_{obs}$ and $\text{Abs}(320)_{obs}$ are measured absorbance at 278, 310 and 320 nm, respectively. If any of the values were higher than 2 OD, the protein solution was diluted with the storage buffer until all the values were below 2 OD. One mg/ml solution would have $\text{Abs}(278)_{cal}$ at 1.27 (extinction coefficient). Therefore the concentration of the protein in a prep can be determined as:

$$\text{enzyme concentration(mg/ml)} = \text{Abs}(278)_{cal}/1.27$$

DNA contamination can be detected by UV absorbance as well. DNA, especially single-stranded DNA, has a high extinction coefficient meaning a very small amount of DNA can register a high OD. Similarly to protein determination, the absorbance at 260 nm was calculated as below:

$$\text{Abs}(260)_{cal} = \text{Abs}(260)_{obs} - 12 \times (\text{Abs}(315)_{obs} - \text{Abs}(320)_{obs})$$

where $\text{Abs}(260)_{cal}$ is calibrated absorbance at 260 nm, and $\text{Abs}(260)_{obs}$, $\text{Abs}(310)_{obs}$ and $\text{Abs}(320)_{obs}$ are measured absorbance at 260, 310 and 320 nm, respectively. The higher the ratio of $\text{Abs}(260)_{cal}$ to $\text{Abs}(278)_{cal}$, the greater the amount of DNA contamination. An $\text{Abs}(278)_{cal}/\text{Abs}(260)_{cal}$ ratio of about 2±10% deviation (1.8 to 2.2) is an acceptable level of DNA contamination in the enzyme prep. The Sso SSB-Tzi polymerase fusion proteins produced by the method described above had an $\text{Abs}(278)_{cal}/\text{Abs}(260)_{cal}$ ratio in the acceptable range described above. The purified Sso-Tzi polymerase fusion protein preparations were also evaluated for the presence of nuclease contamination. Preparations of Sso-Tzi polymerases were found to contain no detectable endonuclease activity and contained little, if any, 5'-exonuclease contamination. 5' exonuclease activity was measured using a DNA substrate radiolabeled at its 5' end by a kinase. The release of the radiolabel was monitored by thin layer chromatography (TLC) after incubation for 1 h at 74° C.

In the double-stranded endonuclease assay, increasing amounts of Sso SSB-Tzi polymerase fusion protein in 1×Tzi buffer with an increased magnesium concentration (45 mM Tris-HCl, pH 8.2, 20 mM KCl, 15 mM (NH$_4$)$_2$SO$_4$, 5 mM MgSO$_4$, 0.14 mg/ml BSA) were added to supercoiled ds φX174 DNA. The ratio of supercoiled circular φX174 DNA to relaxed circular DNA was measured by 1.2% agarose gel electrophoresis. Higher endonuclease activity results in conversion of supercoiled to relaxed circular DNA at an elevated rate. The relaxed circular DNA migrates at a reduced rate on the gel compared to the supercoiled circular DNA.

Example 4

PCR Conditions and Optimization for Sso SSB-Tzi Polymerase Fusion Protein

PCR reactions were prepared in 50 µl reaction volumes, unless indicated otherwise. The typical 50 µl reaction contained five units Tzi High Fidelity polymerase, 1×Tzi buffer (45 mM Tris-HCl, pH 8.2, 20 mM KCl, 15 mM (NH$_4$)$_2$SO$_4$, 1.2 mM MgSO$_4$, 0.14 mg/ml BSA), 0.3 µM of each primer, 0.3 mM dNTP mix, and template concentration that varied from 10-100 pg for plasmids, 10 ng to 1 µg cDNA, and 50-100 ng (genomic DNA). The PCR reactions were set-up at room temperature and run following a standard protocol, unless otherwise stated. Thermocycling was conducted using either the Perkin Elmer GeneAmp PCR System 9600 or the Perkin Elmer GeneAmp PCR System 2400.

Standard PCR Program:

| 94° C. | 2 minutes |
|---|---|
| 35 cycles of | |
| 94° C. | 15 seconds |
| 55° C.-65° C. | 10 seconds |
| 72° C. | 30 to 60 seconds/kb |
| Post PCR elongation | |
| 72° C. | 10 minutes |

Hold at 14° C.

Following the completion of thermocycling, PCR amplification products were mixed with 5 µl of 10× BlueJuice and aliquots (10 µl of total reaction volume per each lane) were analyzed by electrophoresis through an 0.8% agarose gel in 0.5×TBE containing ethidium bromide at a concentration of 0.5 µg/ml. The resulting gels were analyzed visually for specificity and yield among different samples.

Example 5

DNA Polymerase Fidelity Assay

The DNA polymerase fidelity assay is based on streptomycin resistance (Lackovich et al., *Focus* 23:6-7 (2001); Fujii et al., *J. Mol. Biol.* 289:596-601 (1999)). Briefly, pMOL 21 plasmid DNA (4 kb), containing the ampicillin (Apr) and (rpsL) genes, was linearized with Sca I and standard PCR was performed on the linearized product using biotinylated primers. Amplification was done using 5 units of Sso SSB-Tzi polymerase fusion protein. Template DNA (10 ng) was subjected to 35 cycles of amplification. PCR cycling parameters were: 94° C. for 5 min, followed by 35 cycles of 94° C. for 15 s, 58° C. for 10 s, and 72° C. for 5 min, with a 10 minute final elongation at 72° C. The PCR product was streptavidin-magnetic-bead-purified and analyzed on an agarose gel to estimate DNA concentration and template doubling. The purified DNA was ligated with T4 DNA ligase and transformed into MF101 competent cells. Cells were plated on ampicillin plates to determine the total number of transformed cells. Cells were plated on media containing ampicillin and streptomycin to determine the total number of rpsL mutants (i.e., number of streptomycin mutants). Mutation frequency was determined by dividing the total number of rpsL mutants by the total number of transformed cells.

Shown in Table 2 are the relative fidelities of Taq, Tzi (wild type), SsoSSB-Tzi polymerase, and SsoSSB-Tzi polymerase containing and lacking a His6 tag at the C-terminus A relative fidelity of one corresponds to an error rate of $34.13 \pm 9.56 \times 10^{-6}$. The data shown in Table 2 reflect the averages of at least three determinations.

TABLE 2

Fidelity of SsoSSB-Tzi polymerase fusion protein and wild type Tzi polymerase

| Enzyme | Relative Fidelity |
|---|---|
| Taq | 1 |
| Tzi (wild type) | 15 |
| SsoSSB-Tzi polymerase, (His)6 | 52 |
| SsoSSB-Tzi polymerase, Tagless | 53 |

Table 2

Example 6

PCR Amplification with SsoSSB-Tzi Polymerase

SsoSSB-Tzi polymerase was also tested using a range of genomic targets. The targets tested were A) Rhod 462 bp, b) p53 1494 bp, C) Rhod 2497 bp, D) Rhod 3123 bp, and E) Rhod 3871 bp. Standard PCR was used (Example 4) with 100 ng K562 cell DNA as a template. The results are shown in FIG. 1. Both Phusion and iProof had difficulty generating the smallest targets, while Phusion also was unable to amplify the longer 3871 bp fragment. Sso SSB-Tzi polymerase fusion protein had the greatest yields overall, with iProof performing slightly below Sso SSB-Tzi polymerase fusion protein for three of the five targets.

It will be readily apparent to one of ordinary skill in the relevant arts that other suitable modifications and adaptations to the methods and applications described herein may be made without departing from the scope of the invention or any embodiment thereof. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the claims. Having now described the present invention in detail, the same will be more clearly understood by reference to the following examples, which are included herewith for purposes of illustration only and are not intended to be limiting of the invention.

What is claimed is:

1. An isolated or purified single stranded DNA binding protein (SSB)-nucleic acid polymerase fusion protein wherein said SSB comprises amino acids 1 to 150 of SEQ ID NO: 2, wherein said fusion protein comprises at least 50% polymerase activity, 3'-5' exonuclease activity and/or 5'-3' exonuclease activity of the fusion protein shown in SEQ ID NO:2, and wherein the presence of said SSB enhances fidelity of said fusion protein compared to an identical nucleic acid polymerase that is not joined to said SSB.

2. The fusion protein of claim 1 wherein said nucleic acid polymerase is a DNA polymerase.

3. The fusion protein of claim 1, wherein said nucleic acid polymerase is a reverse transcriptase.

4. The fusion protein of claim 1, wherein said nucleic acid polymerase is a thermostable DNA polymerase.

5. The fusion protein of claim 4, wherein said thermostable DNA polymerase is *Thermococcus zilligi* (Tzi) DNA polymerase.

6. The fusion protein of claim 1, wherein said nucleic acid polymerase comprises amino acids 157 to 941 of SEQ ID NO:2.

7. An isolated or purified *Sulfolobus sofataricus* (Sso) SSB-*Thermococcus zilligi* (Tzi) DNA polymerase fusion protein wherein said Sso SSB comprises amino acids 1 to 150 of SEQ ID NO:2 and has at least 50% polymerase activity, 3'-5' exonuclease activity and/or 5'-3' exonuclease activity of the fusion protein shown in SEQ ID NO:2.

8. A fusion polymerase protein that comprises an amino acid sequence that has at least 75% sequence identity to SEQ ID NO:2 and has at least two joined heterologous domains, wherein said heterologous domains comprise:

a. a single-stranded DNA binding protein (SSB) domain comprising amino acids 1 to 150 of SEQ ID NO:2; and b. a polymerase domain, and wherein the relative fidelity of said polymerase fusion protein is enhanced compared to the fidelity of the corresponding full length wild type polymerase protein lacking said SSB domain.

9. The fusion protein of claim 1, wherein said isolated or purified single stranded DNA binding protein (SSB)-nucleic acid polymerase fusion protein comprises no detectable endonuclease activity.

10. The fusion protein of claim 1, wherein said fidelity is enhanced by about 1.2 to 10,000 fold compared to the fidelity of an identical nucleic acid polymerase that is not joined to said SSB.

11. The fusion protein of claim 1, wherein said fusion protein exhibits a reduced misincorporation rate that is less than 90% of the relative misincoporation rate of an identical nucleic acid polymerase that is not joined to said SSB.

12. The fusion protein of claim 4, wherein said thermostable DNA polymerase retains at least 50% of its nucleic acid synthesis activity after bein heated in a nucleic acid synthesis mixture at 90° C. for 30 seconds.

13. The fusion protein of claim 1, wherein said SSB is at the N-terminal and said nucleic acid polymerase is at the C-terminal end of the fusion protein.

14. The fusion protein of claim 1, wherein said SSB is upstream (5') from said nucleic acid polymerase.

15. The fusion protein of claim 1, wherein said SSB and said nucleic acid polymerase are immediately adjacent to each other.

16. The fusion protein of claim 1, wherein said SSB and said nucleic acid polymerase are separated by an amino acid linker.

17. The fusion protein of claim 16, wherein said amino acid linker is between 1 and 100 amino acids in length.

* * * * *

UNITED STATES PATENT AND TRADEMARK OFFICE
CERTIFICATE OF CORRECTION

PATENT NO.         : 8,828,700 B2
APPLICATION NO.    : 12/326048
DATED              : September 9, 2014
INVENTOR(S)        : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 796 days.

Signed and Sealed this
Eighteenth Day of August, 2015

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 2784
<212> TYPE: DNA
<213> ORGANISM: Artificial Sequence
<220> FEATURE:
<223> OTHER INFORMATION: Sequence is a fusion between Sulfolobus
      solfataricus and Thermococcus zilligi

<400> SEQUENCE: 1
atggaagaaa aagtaggtaa tctgaaacca aatatggaaa gcgtaaatgt aaccgtacga      60
gttttggaag caagcgaagc acgtcaaatc cagacaaaga acggtgttcg gacaatcagt     120
```

```
gaggctattg ttggagatga acgggacga gtaaagttaa cattatgggg aaaacatgca      180
ggtagtatca aagaaggtca agtggtaaag attgaaaacg cgtggaccac cgcttttaag     240
ggtcaagtac agttaaatgc tggaagcaaa actaagatcg ctgaagcttc agaagatgga     300
tttccagaat catctcaaat tccagaaaat acaccaacag ctcctcagca aatgcgtgga     360
ggaggacgcg gattccgcgg tggggacgt cggtatggac gacgtggtgg tcgccggcaa      420
gaaaacgaag aaggtgaaga ggagggaagc ggagggggtcg acatgatcct cgatgctgac    480
tacatcaccg aagacggaaa gcccgtcata agggtcttca agaaggaaaa gggcgagttt    540
aagatagact acgacaggga ctttgagccc tacatctacg ccctcctgaa ggacgattcc    600
gccattgagg acatcaagaa gatcaccgcc gagaggcacg gcaccaccgt tagagttacc   660
cgggcggaga gggtgaagaa gaagttcctc ggcaggccgg tggaggtctg gaagctctac   720
ttcacccacc cccaggacgt tcccgcgatc agggacaaaa tcagggagca tccggcggtt   780
gttgacatct acgagtacga catacccttc gcgaagcgct acctcataga caggggctta   840
atccctatgg aggggacga ggagctcagg atgctcgcct tcgacatcga cacgctctac    900
catgaggggg aggagtttgg cgaggggcct atcctgatga taagctacgc cgatgaagag  960
ggggcgcgcg ttatcacctg gaagaatatc gacctcccct acgtggagag cgtttctact  1020
gagaaagaga tgataaagcg cttcctcaag gtaatccagg agaaggatcc ggatgtgctc   1080
ataacctaca acggcgacaa cttcgacttt gcttacctca gaagcgctc agaaacgctc   1140 ggcgtcaagt tcatcctcgg aagggacggg agcgaaccga aaattcagcg catgggcgac  1200
cgctttgcag tggaggtgaa ggggagaata cacttcgacc tctacccggt tataaggagg  1260
actattaacc tccccaccta caccctcgag acagtctacg aggcgatttt cgggcaacca  1320
aaggagaagg tctacgcgga agatagcg cgggcctggg agagcgggga aggcttggaa    1380
agggtggccc gctattccat ggaggacgca aaggcaactt acgaactcgg aaaagagttc  1440
ttcccgatgg aggcccagct ctcgcgcctc gtgggccaga gcctctggga tgtatcgcgc  1500
tcgagcacag gaaacttagt tgagtggttt ctcctgagga aggcctacga gaggaacgag  1560
ctcgcgccaa acaagccgga cgagagggag ttagcaagga gagcggagag ctacgcgggt  1620
ggatatgtca aagagcccga aaaggggctg tgggagaaca tagtctacct cgattacaaa  1680
tctctctacc cctcgataat catcacccac aacgtctccc ctgataccct caacaggag   1740 ggctgtaggg agtacgacgt ggcacctcag gtgggacacc gcttctgcaa ggacttcccg  1800
ggctttatcc cgagcctcct cggggacctt ttggaggaga ggcagaaggt aaagaagaaa  1860
atgaaggcca cggtggaccc gatagagagg aagctcctcg actacaggca acgcgccatc  1920
aagattctgg ccaacagtta ttacggctac tacggctacg caaatgcccg ctggtactgc  1980
agggagtgcg ccgagagcgt taccgcctgg ggcaggcagt atattgaaac cacgatgagg  2040
gaaatagagg agaaatttgg ctttaaagtg ctttacgcgg ataccgacgg tttcttgcc   2100 acgattcccg gagcggacgc cgaaacggtc aaaaagaagg ctaaagaatt cctgaactac  2160 atcaaccca gactgccgg cctgctcgag ctggagtacg agggcttcta caggcgcggc   2220
ttcttcgtga cgaagaagaa gtacgcggtt atagacgagg aggacaagat aacgacgcgc  2280
gggctggaaa tagtaaggcg cgactggagc gagatagcga aggagacgca ggcgagggtt  2340
cttgaggcga tactcaagca cggtgacgtc gaagaggcag taaggattgt caaggaggtg  2400
acggaaaagc tgagtaggta cgaggttcca ccggagaagc tcgtcatcta cgagcagata  2460
```

```
acccgcgacc tgagggacta cagggccacg gggccgcacg tggccgttgc aaaacgcctc    2520
gccgcgaggg ggataaaaat ccggcccggg acggtcataa gctacatagt gctcaaaggc    2580
ccgggaaggg ttggggacag ggcgataccc ttcgacgagt tcgaccctgc aaagcaccgc    2640
tatgatgcgg aatactacat cgagaaccag gttcttccag cggtggagag gattctgagg    2700
gcctttggtt accgcaaaga ggacttgagg tatcagaaga cgaagcaggc cggactgggg    2760
gcgtggctaa aaccgaagac ataa                                           2784
```

<210> SEQ ID NO 2
<211> LENGTH: 929
<212> TYPE: PRT
<213> ORGANISM: Artificial Sequence
<220> FEATURE:
<223> OTHER INFORMATION: Sequence is a fusion between Sulfolobus
      solfataricus and Thermococcus zilligi

<400> SEQUENCE: 2

```
Met Met Glu Glu Lys Val Gly Asn Leu Lys Pro Asn Met Glu Ser Val
1               5                   10                  15

Asn Val Thr Val Arg Val Leu Glu Ala Ser Glu Ala Arg Gln Ile Gln
            20                  25                  30

Thr Lys Asn Gly Val Arg Thr Ile Ser Glu Ala Ile Val Gly Asp Glu
        35                  40                  45

Thr Gly Arg Val Lys Leu Thr Leu Trp Gly Lys His Ala Gly Ser Ile
    50                  55                  60

Lys Glu Gly Gln Val Val Lys Ile Glu Asn Ala Trp Thr Thr Ala Phe
65                  70                  75                  80

Lys Gly Gln Val Gln Leu Asn Ala Gly Ser Lys Thr Lys Ile Ala Glu
                85                  90                  95

Ala Ser Glu Asp Gly Phe Pro Glu Ser Ser Gln Ile Pro Glu Asn Thr
            100                 105                 110

Pro Thr Ala Pro Gln Gln Met Arg Gly Gly Arg Gly Phe Arg Gly
        115                 120                 125

Gly Gly Arg Arg Tyr Gly Arg Arg Gly Gly Arg Gln Glu Asn Glu
    130                 135                 140

Glu Gly Glu Glu Glu Gly Gly Ser Gly Gly Val Asp Met Ile Leu Asp
145                 150                 155                 160

Ala Asp Tyr Ile Thr Glu Asp Gly Lys Pro Val Ile Arg Val Phe Lys
                165                 170                 175

Lys Glu Lys Gly Glu Phe Lys Ile Asp Tyr Asp Arg Asp Phe Glu Pro
            180                 185                 190

Tyr Ile Tyr Ala Leu Leu Lys Asp Asp Ser Ala Ile Glu Asp Ile Lys
        195                 200                 205

Lys Ile Thr Ala Glu Arg His Gly Thr Thr Val Arg Val Thr Arg Ala
    210                 215                 220

Glu Arg Val Lys Lys Lys Phe Leu Gly Arg Pro Val Glu Val Trp Lys
225                 230                 235                 240

Leu Tyr Phe Thr His Pro Gln Asp Val Pro Ala Ile Arg Asp Lys Ile
                245                 250                 255

Arg Glu His Pro Ala Val Val Asp Ile Tyr Glu Tyr Asp Ile Pro Phe
            260                 265                 270

Ala Lys Arg Tyr Leu Ile Asp Arg Gly Leu Ile Pro Met Glu Gly Asp
        275                 280                 285

Glu Glu Leu Arg Met Leu Ala Phe Asp Ile Glu Thr Leu Tyr His Glu
    290                 295                 300
```

```
Gly Glu Glu Phe Gly Glu Gly Pro Ile Leu Met Ile Ser Tyr Ala Asp
305                 310                 315                 320

Glu Glu Gly Ala Arg Val Ile Thr Trp Lys Asn Ile Asp Leu Pro Tyr
            325                 330                 335

Val Glu Ser Val Ser Thr Glu Lys Glu Met Ile Lys Arg Phe Leu Lys
                340                 345                 350

Val Ile Gln Glu Lys Asp Pro Asp Val Leu Ile Thr Tyr Asn Gly Asp
            355                 360                 365

Asn Phe Asp Phe Ala Tyr Leu Lys Lys Arg Ser Glu Thr Leu Gly Val
370                 375                 380

Lys Phe Ile Leu Gly Arg Asp Gly Ser Glu Pro Lys Ile Gln Arg Met
385                 390                 395                 400

Gly Asp Arg Phe Ala Val Glu Val Lys Gly Arg Ile His Phe Asp Leu
                405                 410                 415

Tyr Pro Val Ile Arg Arg Thr Ile Asn Leu Pro Thr Tyr Thr Leu Glu
            420                 425                 430

Thr Val Tyr Glu Ala Ile Phe Gly Gln Pro Lys Glu Lys Val Tyr Ala
            435                 440                 445

Glu Glu Ile Ala Arg Ala Trp Glu Ser Gly Gly Leu Glu Arg Val
450                 455                 460

Ala Arg Tyr Ser Met Glu Asp Ala Lys Ala Thr Tyr Glu Leu Gly Lys
465                 470                 475                 480

Glu Phe Phe Pro Met Glu Ala Gln Leu Ser Arg Leu Val Gly Gln Ser
                485                 490                 495

Leu Trp Asp Val Ser Arg Ser Ser Thr Gly Asn Leu Val Glu Trp Phe
                500                 505                 510

Leu Leu Arg Lys Ala Tyr Glu Arg Asn Glu Leu Ala Pro Asn Lys Pro
            515                 520                 525

Asp Glu Arg Glu Leu Ala Arg Arg Ala Glu Ser Tyr Ala Gly Gly Tyr
            530                 535                 540

Val Lys Glu Pro Glu Lys Gly Leu Trp Glu Asn Ile Val Tyr Leu Asp
545                 550                 555                 560

Tyr Lys Ser Leu Tyr Pro Ser Ile Ile Ile Thr His Asn Val Ser Pro
                565                 570                 575

Asp Thr Leu Asn Arg Glu Gly Cys Arg Glu Tyr Asp Val Ala Pro Gln
            580                 585                 590

Val Gly His Arg Phe Cys Lys Asp Phe Pro Gly Phe Ile Pro Ser Leu
        595                 600                 605

Leu Gly Asp Leu Leu Glu Glu Arg Gln Lys Val Lys Lys Met Lys
            610                 615                 620

Ala Thr Val Asp Pro Ile Glu Arg Lys Leu Leu Asp Tyr Arg Gln Arg
625                 630                 635                 640

Ala Ile Lys Ile Leu Ala Asn Ser Tyr Tyr Gly Tyr Tyr Gly Tyr Ala
                645                 650                 655

Asn Ala Arg Trp Tyr Cys Arg Glu Cys Ala Glu Ser Val Thr Ala Trp
                660                 665                 670

Gly Arg Gln Tyr Ile Glu Thr Thr Met Arg Glu Ile Glu Glu Lys Phe
            675                 680                 685

Gly Phe Lys Val Leu Tyr Ala Asp Thr Asp Gly Phe Phe Ala Thr Ile
        690                 695                 700

Pro Gly Ala Asp Ala Glu Thr Val Lys Lys Lys Ala Lys Glu Phe Leu
705                 710                 715                 720
```

-continued

```
Asn Tyr Ile Asn Pro Arg Leu Pro Gly Leu Leu Glu Leu Glu Tyr Glu
                725                 730                 735

Gly Phe Tyr Arg Arg Gly Phe Phe Val Thr Lys Lys Lys Tyr Ala Val
            740                 745                 750

Ile Asp Glu Glu Asp Lys Ile Thr Thr Arg Gly Leu Glu Ile Val Arg
        755                 760                 765

Arg Asp Trp Ser Glu Ile Ala Lys Glu Thr Gln Ala Arg Val Leu Glu
    770                 775                 780

Ala Ile Leu Lys His Gly Asp Val Glu Glu Ala Val Arg Ile Val Lys
785                 790                 795                 800

Glu Val Thr Glu Lys Leu Ser Arg Tyr Glu Val Pro Pro Glu Lys Leu
                805                 810                 815

Val Ile Tyr Glu Gln Ile Thr Arg Asp Leu Arg Asp Tyr Arg Ala Thr
                820                 825                 830

Gly Pro His Val Ala Val Ala Lys Arg Leu Ala Ala Arg Gly Ile Lys
            835                 840                 845

Ile Arg Pro Gly Thr Val Ile Ser Tyr Ile Val Leu Lys Gly Pro Gly
    850                 855                 860

Arg Val Gly Asp Arg Ala Ile Pro Phe Asp Glu Phe Asp Pro Ala Lys
865                 870                 875                 880

His Arg Tyr Asp Ala Glu Tyr Tyr Ile Glu Asn Gln Val Leu Pro Ala
            885                 890                 895

Val Glu Arg Ile Leu Arg Ala Phe Gly Tyr Arg Lys Glu Asp Leu Arg
            900                 905                 910

Tyr Gln Lys Thr Lys Gln Ala Gly Leu Gly Ala Trp Leu Lys Pro Lys
        915                 920                 925

Thr
```